(12) United States Patent
Cronenberg

(10) Patent No.: US 11,364,336 B2
(45) Date of Patent: Jun. 21, 2022

(54) MICROINFUSER WITH AUTOMATIC NEEDLE RETRACTION

(71) Applicant: Becton, Dickinson and Company, Franklin Lakes, NJ (US)

(72) Inventor: Richard Cronenberg, Mahwah, NJ (US)

(73) Assignee: Becton, Dickinson and Company, Franklin Lakes, NJ (US)

( * ) Notice: Subject to any disclaimer, the term of this patent is extended or adjusted under 35 U.S.C. 154(b) by 263 days.

(21) Appl. No.: 16/523,778

(22) Filed: Jul. 26, 2019

(65) Prior Publication Data

US 2019/0344012 A1 Nov. 14, 2019

Related U.S. Application Data

(63) Continuation of application No. 14/391,666, filed as application No. PCT/US2013/035925 on Apr. 10, 2013, now Pat. No. 10,406,280.

(Continued)

(51) Int. Cl.
*A61M 5/142* (2006.01)
*A61M 5/20* (2006.01)
*A61M 5/145* (2006.01)

(52) U.S. Cl.
CPC .......... *A61M 5/14248* (2013.01); *A61M 5/20* (2013.01); *A61M 5/2033* (2013.01);

(Continued)

(58) Field of Classification Search
CPC .... A61M 5/20; A61M 5/2033; A61M 5/1454; A61M 5/14248; A61M 2205/582;

(Continued)

(56) References Cited

U.S. PATENT DOCUMENTS 5,312,364 A 5/1994 Jacobs
5,571,133 A 11/1996 Yoon (Continued)

FOREIGN PATENT DOCUMENTS

AU 2010207762 A1 9/2010
JP 1-130743 U 9/1989

(Continued)

*Primary Examiner* — Tiffany Legette
(74) *Attorney, Agent, or Firm* — Dickinson Wright PLLC

(57) ABSTRACT

A device for delivering a fluid includes a housing defining an interior space and having a bottom surface configured for contacting a patient. The bottom surface defines a needle opening. The device also includes a reservoir disposed within the interior space of the housing for containing a fluid therein, a needle carrier disposed within the housing, and an injection needle supported by the needle carrier and defining a lumen. The lumen of the injection needle is configured to be placed in fluid communication with the reservoir. The injection needle is transitionable from an initial position in which the injection needle is disposed within the housing, to a use position in which the injection needle extends through the needle opening, and a substantially shielded position in which the injection needle is disposed within the housing and the lumen of the needle is blocked by a portion of the housing.

8 Claims, 23 Drawing Sheets

Related U.S. Application Data

(60) Provisional application No. 61/624,026, filed on Apr. 13, 2012.

(52) U.S. Cl.
CPC . *A61M 5/1454* (2013.01); *A61M 2005/14252* (2013.01); *A61M 2005/14256* (2013.01); *A61M 2005/206* (2013.01); *A61M 2205/582* (2013.01); *A61M 2205/584* (2013.01); *A61M 2205/585* (2013.01)

(58) Field of Classification Search
CPC ...... A61M 2205/584; A61M 2205/585; A61M 2005/14252; A61M 2005/14256
See application file for complete search history.

(56) References Cited

U.S. PATENT DOCUMENTS

| | | |
|---|---|---|
| 7,637,891 B2 | 12/2009 | Wall |
| 2001/0025168 A1 | 9/2001 | Gross et al. |
| 2002/0123740 A1 | 9/2002 | Flaherty |
| 2008/0097330 A1 | 4/2008 | King |
| 2009/0130639 A1 | 5/2009 | Skinner |
| 2010/0010454 A1* | 1/2010 | Marshall ............. A61M 5/2033 604/208 |
| 2010/0145282 A1 | 6/2010 | Hansen |
| 2010/0168683 A1 | 7/2010 | Cabiri |
| 2011/0166512 A1* | 7/2011 | Both ................. A61M 5/14248 604/67 |
| 2012/0130207 A1* | 5/2012 | O'dea ............... A61M 37/0015 600/309 |
| 2013/0110049 A1 | 5/2013 | Cronenberg et al. |
| 2016/0089056 A1 | 3/2016 | Limaye et al. |

FOREIGN PATENT DOCUMENTS

| | | |
|---|---|---|
| JP | H04256757 | 9/1992 |
| JP | 2002505601 | 2/2002 |
| JP | 2004501721 | 1/2004 |
| JP | 2005538773 | 12/2005 |
| WO | WO-2004024211 A2 | 3/2004 |
| WO | WO-2005/018705 | 3/2005 |
| WO | WO-2005018703 A2 | 3/2005 |
| WO | WO-2011075105 A1 | 6/2011 |
| WO | WO-2011133823 A1 | 10/2011 |
| WO | WO-2011146166 A1 | 11/2011 |
| WO | WO-2012025639 A1 | 3/2012 |

* cited by examiner

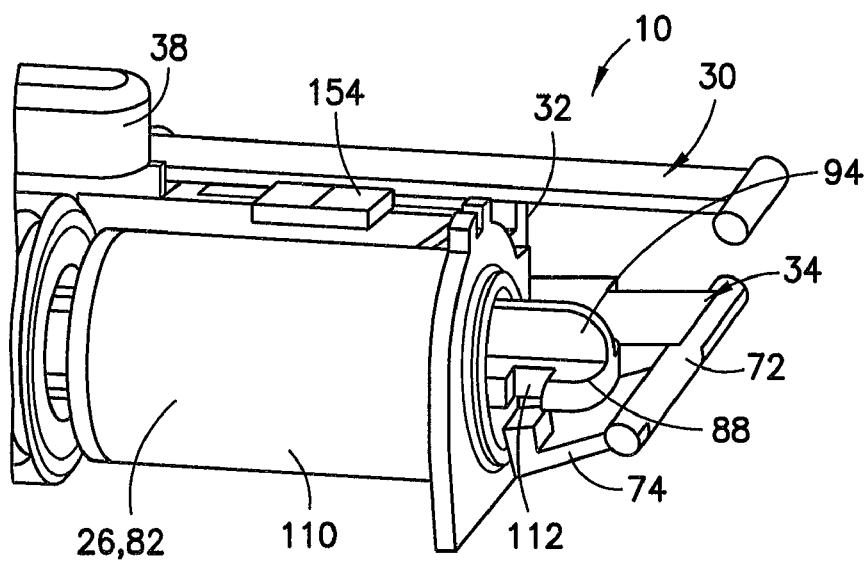
FIG.15
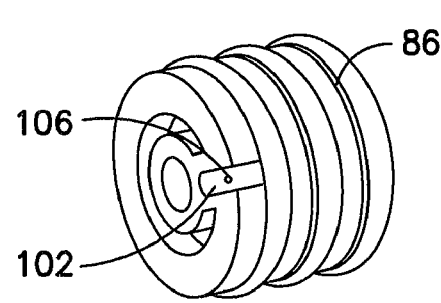 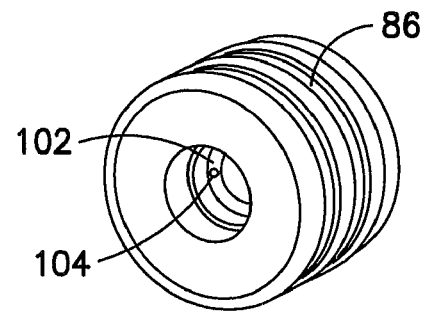
FIG.17  FIG.18

MICROINFUSER WITH AUTOMATIC NEEDLE RETRACTION

RELATED APPLICATIONS

This application is a continuation of U.S. patent application Ser. No. 14/391,666, filed on Oct. 9, 2014, which is the U.S. national stage of International Patent Application No. PCT/US2013/035925, filed on Apr. 10, 2013, which claims priority to U.S. Provisional Application No. 61/624,026, filed on Apr. 13, 2012, the disclosures of all of which are incorporated herein by reference in their entirety.

BACKGROUND OF THE INVENTION

Field of the Invention

The present invention relates generally to a device for delivering a fluid into the body of a patient by injection and, more particularly, to an infusing device with a mechanism for automatically retracting a needle after injection.

Description of Related Art

Various types of automatic injection devices have been developed to allow drug solutions and other liquid therapeutic preparations to be administered by untrained personnel or to be self-injected. Generally, these devices include a reservoir that is pre-filled with the liquid therapeutic preparation, and some type of automatic needle-injection mechanism (usually of the spring-loaded type) that can be triggered by the user. When the volume of fluid or drug to be administered is generally below a certain volume, such as 1 mL, an auto injector is typically used, which typically has an injection time of about 10 to 15 seconds. When the volume of fluid or drug to be administered is above 1 mL, the injection time generally becomes longer resulting in difficulties for the patient to maintain contact between the device and the target area of the patient's skin. Further, as the volume of drug to be administered becomes larger, increasing the time period for injection becomes desirable. The traditional method for a drug to be injected slowly into a patient is to initiate an IV and inject the drug into the patient's body slowly. Such a procedure is typically performed in a hospital or outpatient setting.

Certain devices allow for self-injection in a home setting and are capable of gradually infusing a liquid therapeutic preparation into the skin of a patient. In some cases, these devices are small enough (both in height and in overall size) to allow them to be "worn" by a patient while the liquid therapeutic preparation is being infused into the patient. These devices typically include a pump or other type of discharge mechanism to force the liquid therapeutic preparation to flow out of a reservoir and into the injection or infusion needle. Such devices also typically include a valve or flow control mechanism to cause the liquid therapeutic preparation to begin to flow at the proper time and a triggering mechanism to initiate the injection. As with conventional syringes, needle-stick injuries with self-injection infusing devices are a concern.

SUMMARY OF THE INVENTION

In one embodiment, a device for delivering a fluid includes a housing defining an interior space and having a bottom surface configured for contacting a patient. The bottom surface defines a needle opening. The device also includes a reservoir disposed within the interior space of the housing for containing a fluid therein, a needle carrier disposed within the housing, and an injection needle supported by the needle carrier and defining a lumen. The lumen of the injection needle is configured to be placed in fluid communication with the reservoir. The injection needle is transitionable from an initial position in which the injection needle is disposed within the housing, to a use position in which the injection needle extends through the needle opening, and a substantially shielded position in which the injection needle is disposed within the housing and the lumen of the needle is blocked by a portion of the housing.

The device may also include a needle actuator having a first ramp portion having an inclined section and a level section with the level section being generally parallel to the bottom surface of the housing. The needle carrier may include a first engagement for contacting the inclined section of the first ramp portion to transition the injection needle from the initial position to the use position. The needle actuator may also include a second ramp portion having an inclined section and a level section being generally parallel to the bottom surface of the housing and the needle carrier may include a second engagement for contacting the inclined section of the second ramp portion to transition the injection needle from the use position to the shielded position. The device may include a pad disposed within the housing, where the lumen of the injection needle is blocked by the pad when the injection needle is in the shielded position. The needle actuator may be configured to drive the injection needle into the pad when the injection needle is transitioned from the use position to the shielded position. At least a portion of the pad may be received by the needle actuator in the shielded position.

The reservoir may be configured to automatically supply fluid to the injection needle after the injection needle is transitioned from the initial position to the use position. A needle actuator may be configured to engage the needle carrier to transition the injection needle from the initial position, to the use position, and the shielded position. The reservoir may comprise a syringe assembly including a syringe barrel for containing a fluid therein, a stopper disposed within the syringe barrel, and a plunger configured to advance the stopper within the syringe barrel to expel the fluid therefrom. The device may include a plunger stop engaged with the plunger when the injection needle is in the initial position, wherein the plunger stop is configured to engage the needle carrier and release the plunger stop from the plunger when the injection needle is transitioned from the initial position to the use position. The device may include a needle stop configured to restrict movement of the injection needle from the use position to the shielded position until a predetermined amount of fluid has been dispensed from the reservoir. The needle stop may include a rotatable body which engages the needle actuator and the plunger when the injection needle is in the use position with the needle stop disengaging from the plunger when the injection needle is transitioned from the use position to the shielded position.

The device may also include an activation button, wherein deployment of the activation button allows the injection needle to transition from the initial position to the use position. The device may be provided with an indicator for indicating when the injection needle is in the initial position, the use position, and the shielded position.

In a further embodiment, a device for delivering a fluid includes a housing defining an interior space and having a bottom surface configured for contacting a patient. The bottom surface defines a needle opening. The device further includes a reservoir disposed within the interior space of the housing for containing a fluid therein, a needle carrier disposed within the housing, and an injection needle supported by the needle carrier and defining a lumen. The lumen of the injection needle is configured to be placed in fluid communication with the reservoir, wherein the injection needle is transitionable from an initial position in which the injection needle is disposed within the housing, to a use position in which the injection needle extends through the needle opening, and a substantially shielded position in which the injection needle is disposed within the housing. The device also includes an indicator for indicating when the injection needle is in the initial position, the use position, and the shielded position.

The housing may include at least one indicator lens, where the indicator is visible from an exterior of the housing via the indicator lens. The indicator may provide a visual and tactile indication of the position of the injection needle. The indicator may include an indicator post with the housing defining an indicator opening. The indicator post is disposed within the housing when the injection needle is in the initial position and the use position and extends through the indicator opening when the injection needle is in the shielded position.

In another embodiment, a device for delivering a fluid includes a housing defining an interior space and having a bottom surface configured for contacting a patient. The bottom surface defines a needle opening. The device further includes a reservoir disposed within the interior space of the housing for containing a fluid therein, a needle carrier disposed within the housing, an activation member, and an injection needle supported by the needle carrier and defining a lumen. The lumen of the injection needle is configured to be placed in fluid communication with the reservoir. Deployment of the activation member causes the injection needle to transition from an initial position in which the injection needle is disposed within the housing, to a use position in which the injection needle extends through the needle opening, and a substantially shielded position in which the injection needle is disposed within the housing.

The device may include a needle actuator configured to engage the needle carrier to transition the injection needle from the initial position, to the use position, and the shielded position. The device may also include a needle stop configured to restrict movement of the injection needle from the use position to the shielded position until a predetermined amount of fluid has been dispensed from the reservoir. The activation member may engage the needle actuator when the injection needle is in the initial position. The needle stop may engage the needle actuator when the injection needle is in the use position, and the needle stop may be disengaged from the needle actuator when the injection needle is in the shielded position.

Further details and advantages of the invention will become clear upon reading the following detailed description in conjunction with the accompanying drawing figures, wherein like parts are designated with like reference numerals throughout.

BRIEF DESCRIPTION OF THE DRAWINGS

FIG. 15 is a partial perspective view of the device of FIG. 1 showing a second position of a plunger stop in accordance with an embodiment of the present invention.

FIG. 17 is a perspective view of a stopper in accordance with an embodiment of the present invention.

FIG. 18 is a perspective view of a stopper in accordance with an embodiment of the present invention.

DESCRIPTION OF PREFERRED EMBODIMENTS

Figure 1:
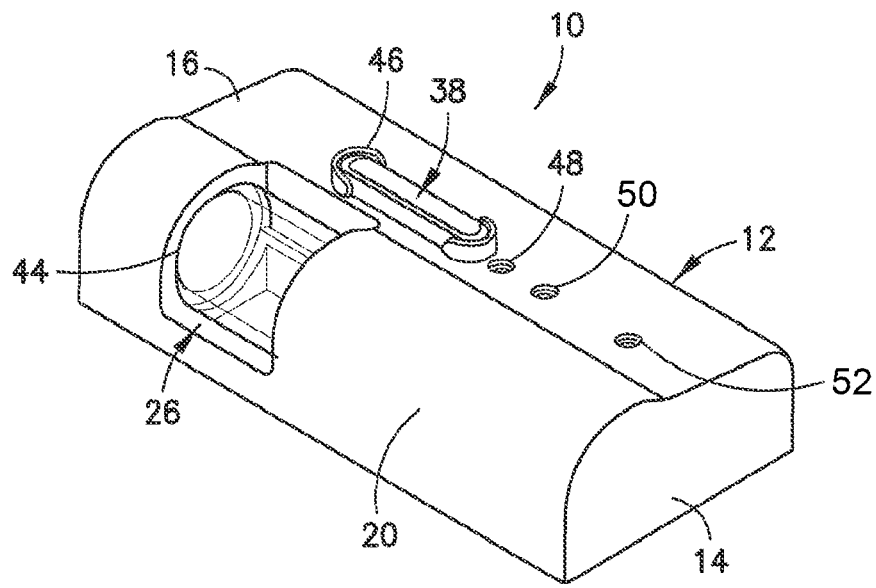
FIG. 1 is a perspective view of a device for delivering a fluid into a patient by injection in accordance with an embodiment of the present invention.
Figure 2:
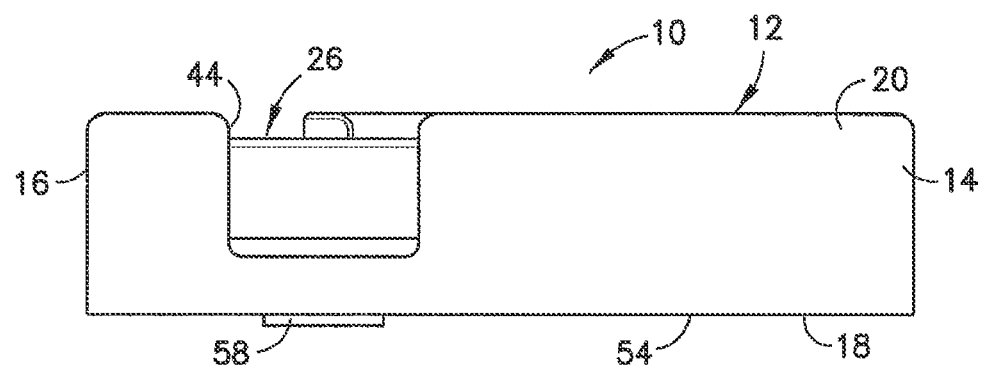
FIG. 2 is a front view of the device of FIG. 1 in accordance with an embodiment of the present invention.
Figure 3:
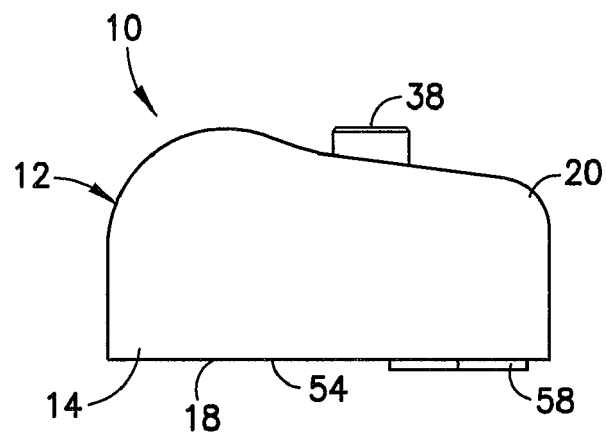
FIG. 3 is a right view of the device of FIG. 1 in accordance with an embodiment of the present invention.
Figure 4:
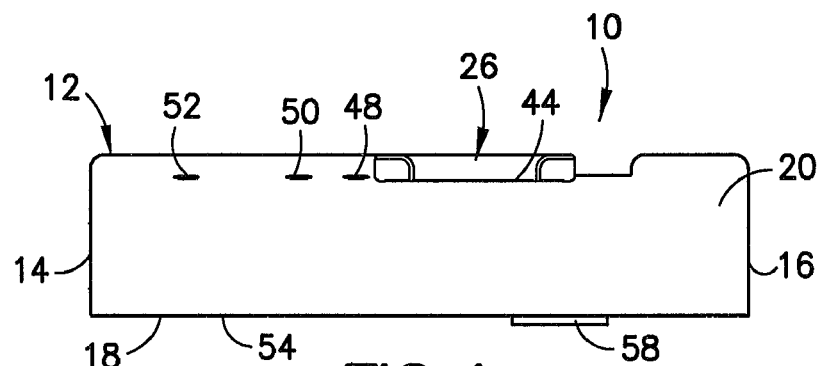
FIG. 4 is a rear view of the device of FIG. 1 in accordance with an embodiment of the present invention.
Figure 5:
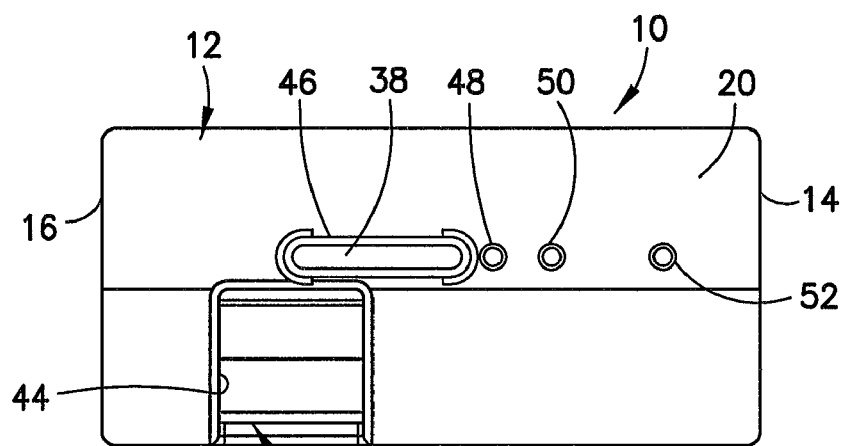
FIG. 5 is a top view of the device of FIG. 1 in accordance with an embodiment of the present invention.

For purposes of the description hereinafter, spatial orientation terms, if used, shall relate to the referenced embodiment as it is oriented in the accompanying drawing figures or otherwise described in the following detailed description. However, it is to be understood that the embodiments described hereinafter may assume many alternative variations and embodiments. It is also to be understood that the specific devices illustrated in the accompanying drawing figures and described herein are simply exemplary and should not be considered as limiting.

Referring to FIGS. 1-16, a device for delivering a fluid into a patient by injection 10 is shown. The device 10 generally includes a housing 12 having a first end 14 and a second end 16. The housing 12 includes a bottom portion 18 and a top cover 20 that define an interior space 22. The device further includes a reservoir 26, an injection needle 28, a needle carrier 30, a needle actuator 32, a plunger stop 34, a needle stop 36, and an activation button 38 that are accommodated by the housing 12. The device 10 is utilized to inject a drug or medicament into a patient and is configured to be engaged with, such as mounted onto, a patient's skin for self-administration. Any form of medicament, e.g., liquid or slurry, including one or more pharmaceutically-active agents, may be administered by the device 10.

Figure 6:
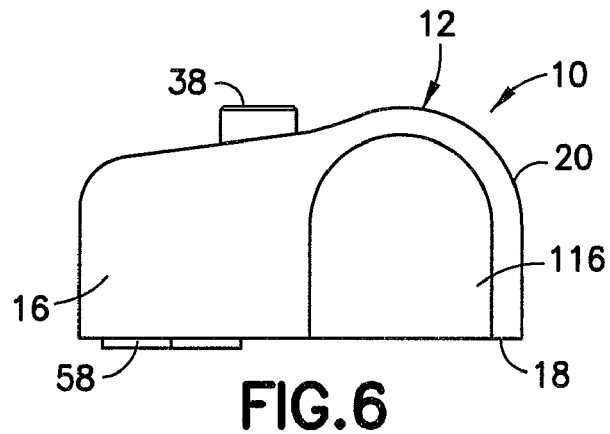
FIG. 6 is a left view of the device of FIG. 1 in accordance with an embodiment of the present invention.
Figure 7:
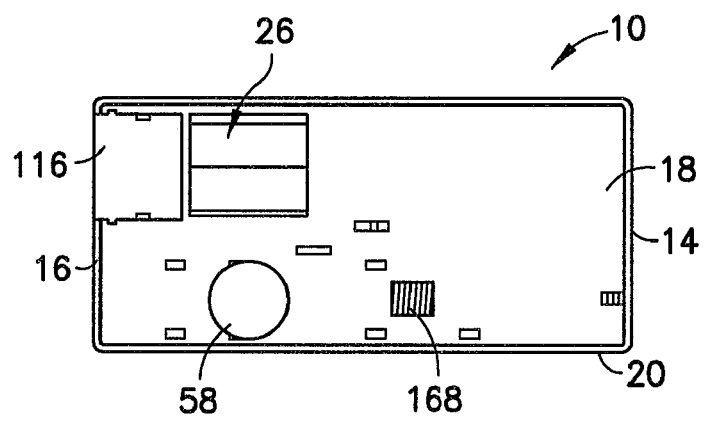
FIG. 7 is a bottom view of the device of FIG. 1 in accordance with an embodiment of the present invention.
Figure 8:
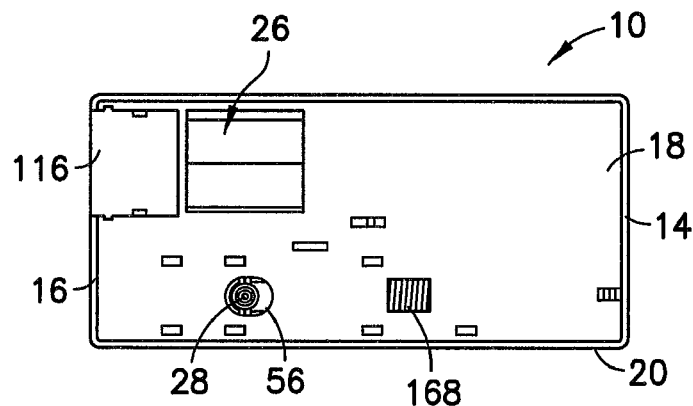
FIG. 8 is a bottom view of the device of FIG. 1 showing a needle cap removed in accordance with an embodiment of the present invention.

Referring to FIGS. 1-9, the top cover 20 of the housing 12 includes a reservoir opening 44, a button opening 46, a first indicator lens 48, a second indicator lens 50, and third indicator lens 52. The reservoir opening 44 allows for the visual inspection of the reservoir 26 without removing the top cover 20. The button opening 46 receives the activation button 38 with a portion of the activation button 38 extending through the opening 46. The first, second, and third indicator lenses 48, 50, 52 may allow visual inspection of a portion of the needle actuator 32 to provide an indication of the status of the device 10. In particular, the first, second, and third indicator lenses 48, 50, 52 may be made from a transparent material to allow visual inspection of the interior space 22 of the housing 12, as will be described herein. The bottom portion 18 of the housing 12 has a bottom surface 54 that defines a needle opening 56. The bottom surface 54 is configured to be placed into contact with a target surface (not shown) of a patient. As shown in FIG. 7, a needle cap 58 is received by the needle opening 56 in an initial pre-use position to shield the injection needle 28, as shown in FIG. 8, prior to use.

Figure 10:
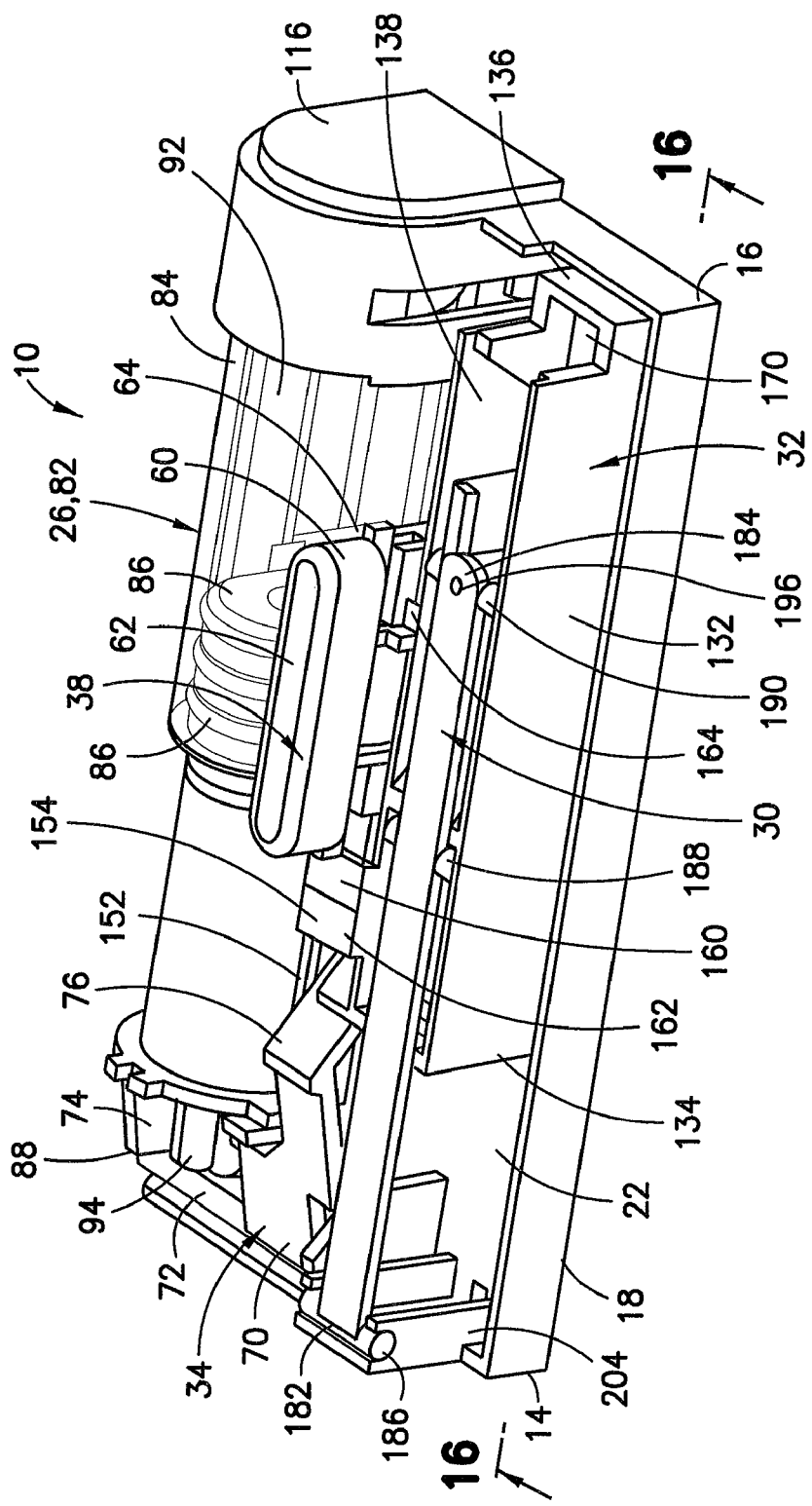
FIG. 10 is a perspective view of the device of FIG. 1 showing detail of an activation button in accordance with an embodiment of the present invention.
Figure 11:
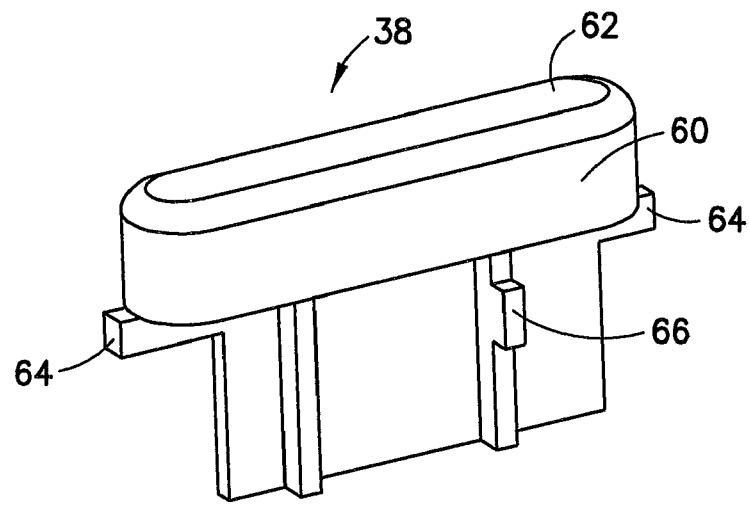
FIG. 11 is a perspective view of an activation button in accordance with an embodiment of the present invention.
Figure 12:
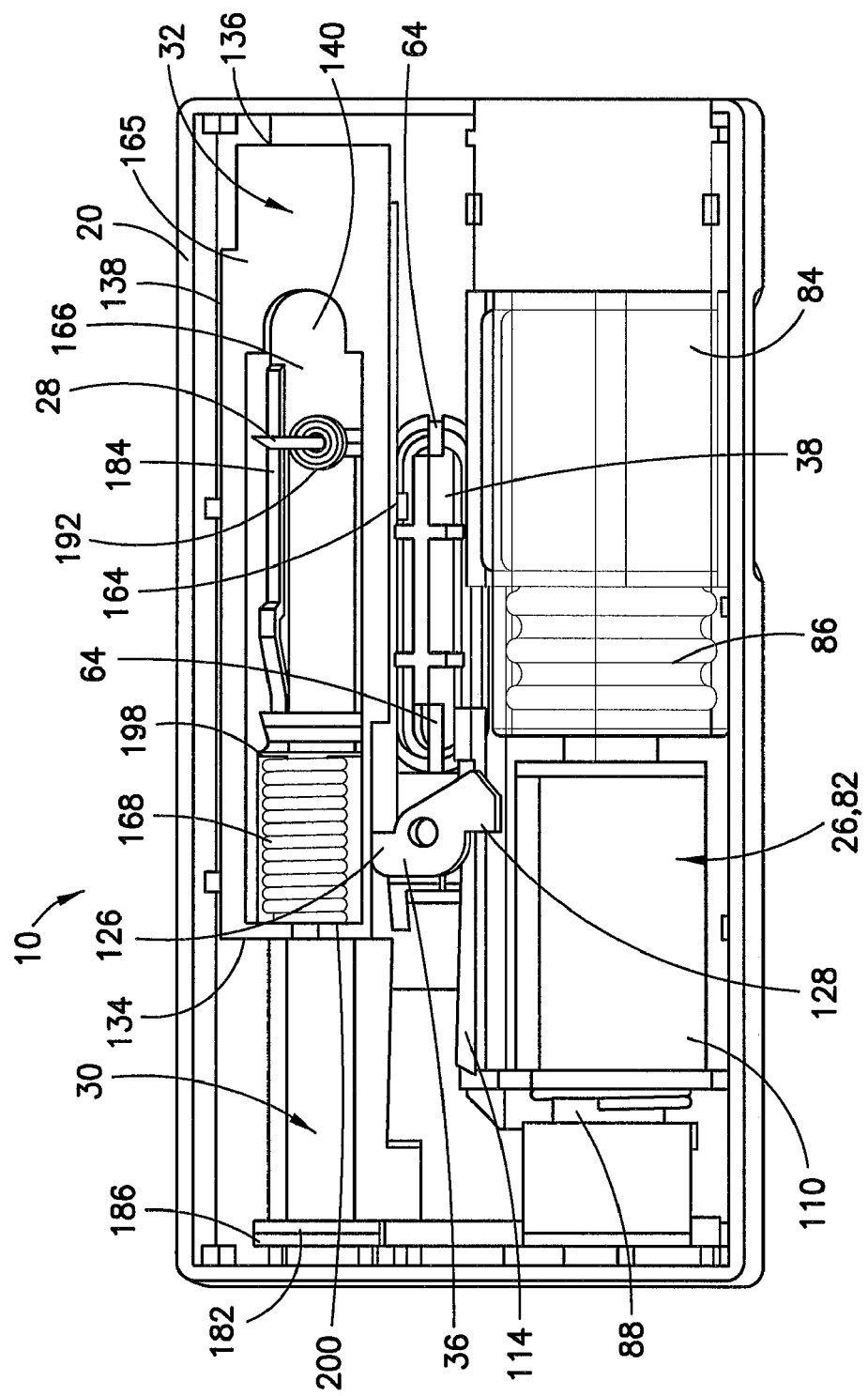
FIG. 12 is a bottom view of the device of FIG. 1 showing a bottom portion of the housing removed in accordance with an embodiment of the present invention.

Referring to FIGS. 10-12, the activation button 38 includes a body 60 having a top surface 62 for engagement by a user. The top surface 62 of the body 60 extends through the button opening 46 of the housing 12. A pair of tab members 64 extends outwardly from the body 60 and is received by the top cover 20 of the housing 12. The body 60 of the activation button 38 includes a lock member 66 extending toward the needle actuator 32. The activation button 38 is moveable within the housing 12 and is configured to restrict movement of the needle actuator 32. In particular, when the activation button 38 is in the position shown in FIG. 10, the lock member 66 of the activation button 38 will be in interference engagement with the needle actuator 32 to restrict forward movement of the needle actuator 32. Pressing downward on the activation button 38 will release the lock member 66 from the needle actuator 32 and start the operation of the device 10, which will be discussed in more detail below.

Figure 14:
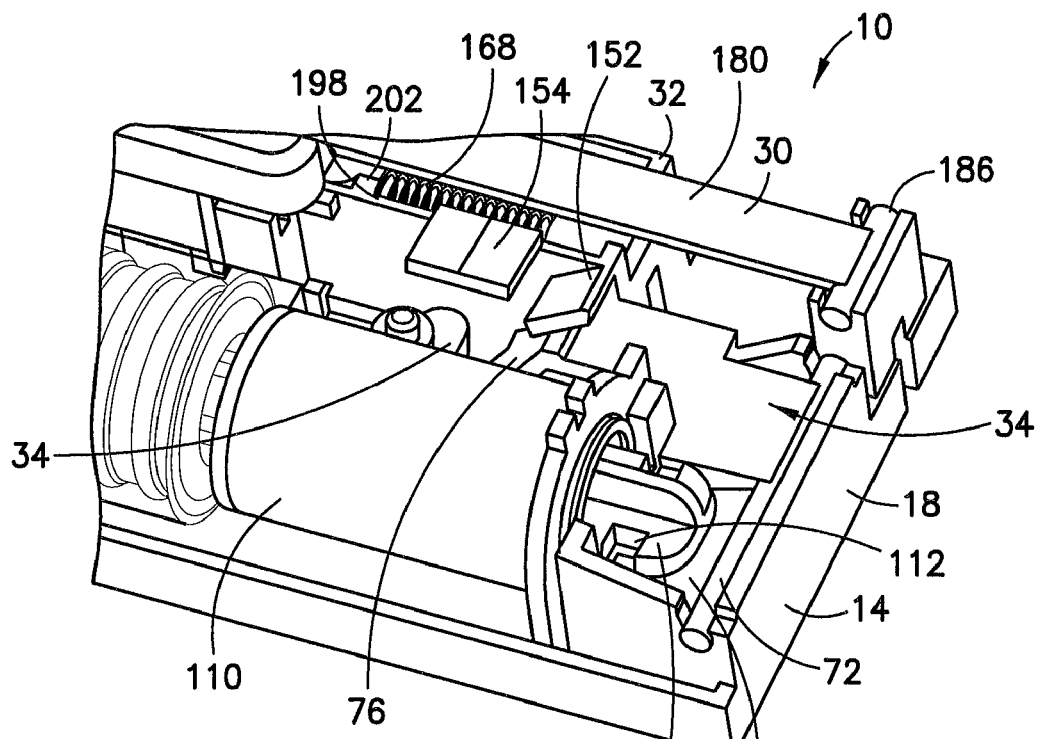
FIG. 14 is an enlarged perspective view of the device of FIG. 1 showing a second position of a plunger stop in accordance with an embodiment of the present invention.
Figure 13:
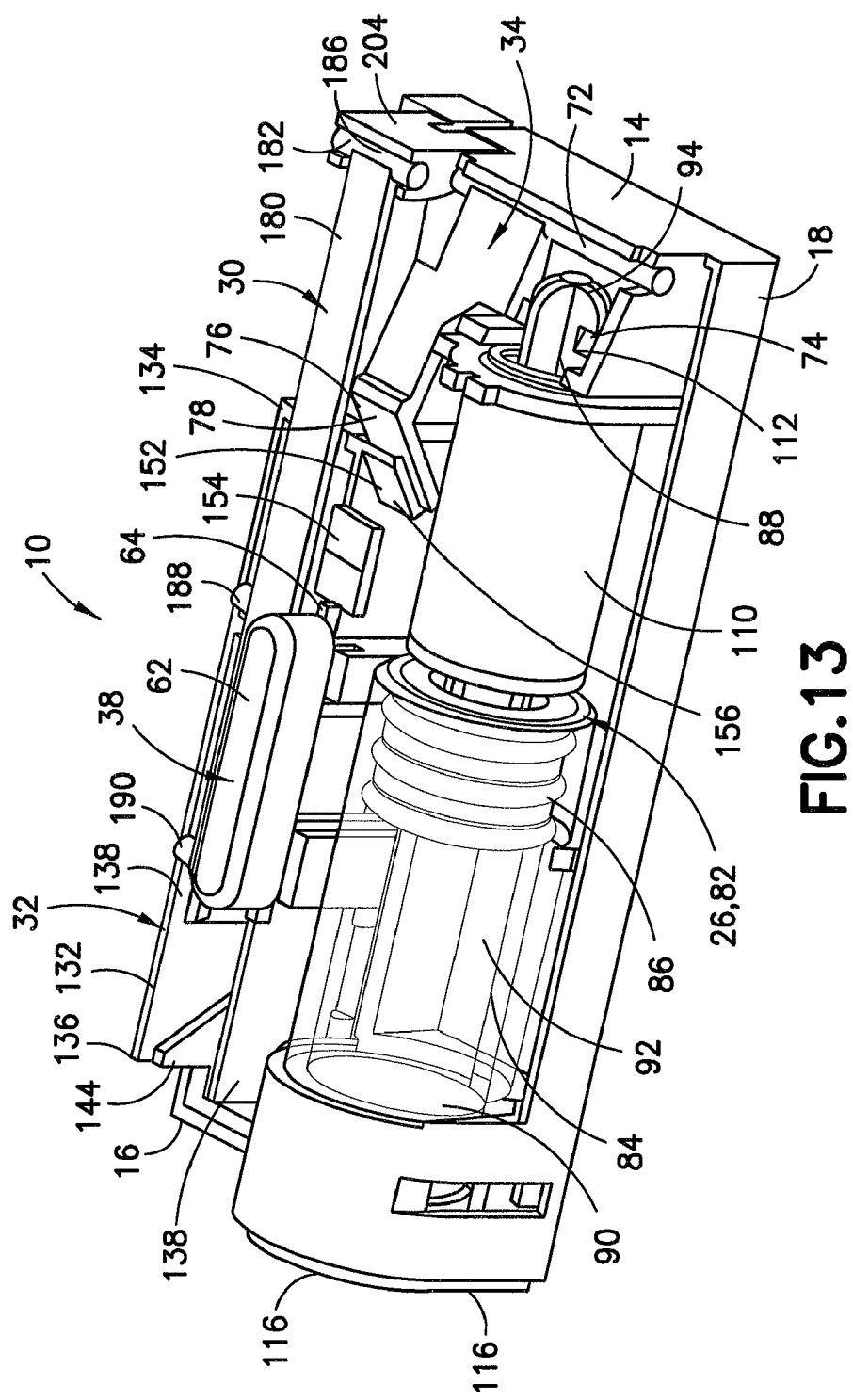
FIG. 13 is a perspective view of the device of FIG. 1 showing a first position of a plunger stop in accordance with an embodiment of the present invention.
Figure 16:
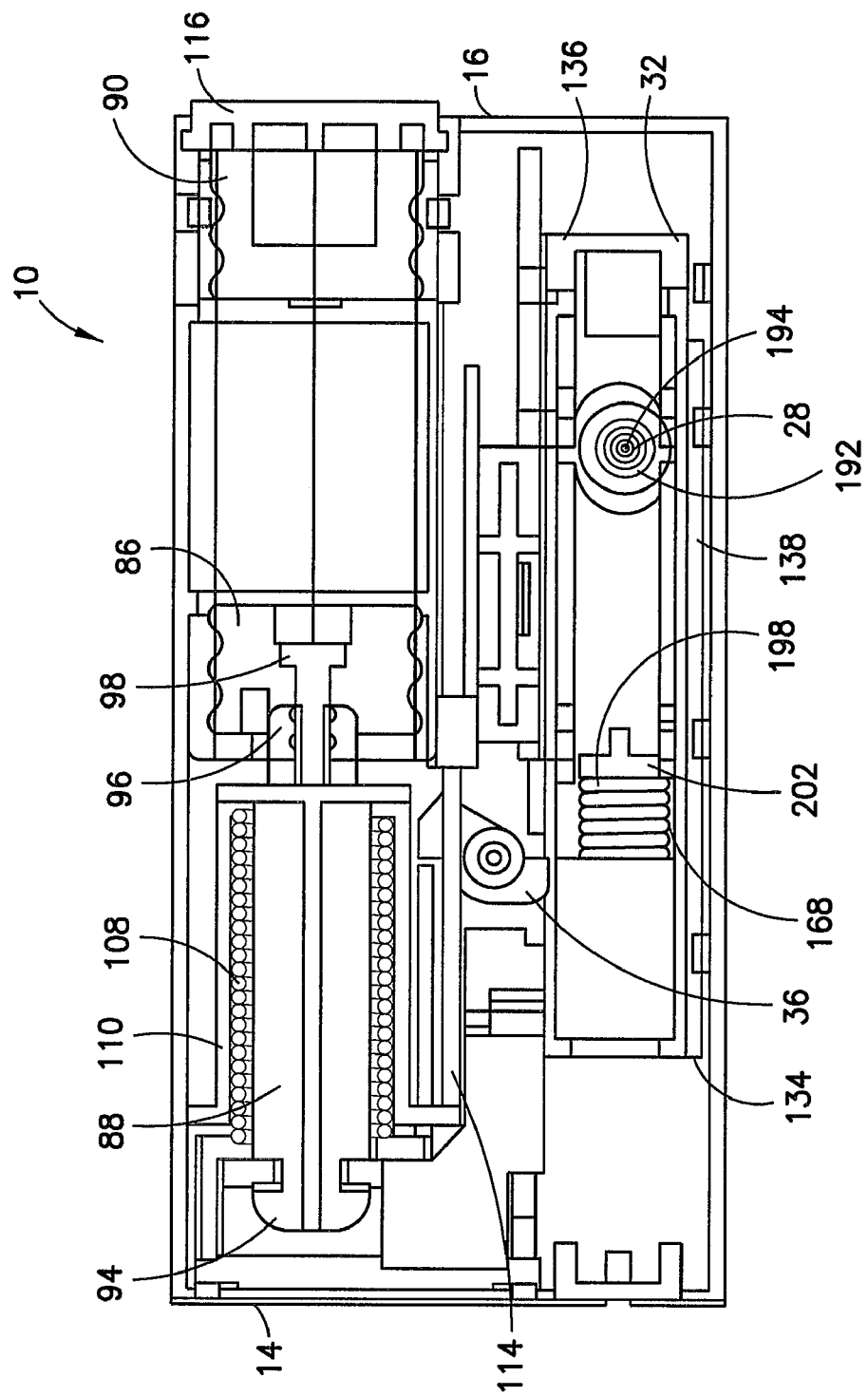
FIG. 16 is a cross-sectional view taken along line 16-16 of FIG. 10 in accordance with an embodiment of the present invention.

Referring to FIGS. 13-15, the plunger stop 34 includes a body 70 having an attachment portion 72, a plunger engagement portion 74, and an actuator tab 76. The attachment portion 72 is configured to be rotatably secured to the bottom portion 18 of the housing 12. The plunger engagement portion 74 extends from the attachment portion 72 and is configured to engage the reservoir 26 as discussed in more detail below. The actuator tab 76 extends from the attachment portion 72 and includes an inclined planar surface 78 that is configured to engage a correspondingly shaped portion of the needle actuator 32. The plunger stop 34 has a first position, as shown in FIG. 13, and a second position, as shown in FIGS. 14 and 15.

Referring to FIGS. 13 and 16-18, the reservoir 26 is embodied as a syringe assembly 82 having a syringe barrel 84, a valve stopper 86, a plunger 88, and a fill stopper 90, although other suitable reservoirs may be utilized. The syringe assembly 82 is configured to be disposed within the housing 12 and arranged along a longitudinal axis of the housing 12. The syringe barrel 84 defines an interior space 92 for receiving a fluid therein and also receives the valve stopper 86 and fill stopper 90. The plunger 88 includes a first end 94 and a second end 96 with the second end 96 of the plunger 88 engaged with the valve stopper 86. A valve member 98 is received by the valve stopper 86 and is moveable between an open position and a closed position. The valve stopper 86 includes a passageway 102 having an inlet 104 and an outlet 106 generally extending through the valve stopper 86. The passageway 102 of the valve stopper 86 is in fluid communication with the interior space 92 of the syringe barrel 84 when the valve member 98 is in the open position. A tube (not shown) extends from the outlet 106 of the passageway 102 to the injection needle 28. The syringe assembly 82 further includes a plunger spring 108 configured to bias the valve stopper 86 towards the fill stopper 90 such that fluid within the syringe barrel 84 is displaced through the passageway 102 of the valve stopper 86. A plunger guard 110 is disposed over the plunger spring 108. The first end 94 of the plunger 88 defines a notch 112 configured to engage the plunger engagement portion 74 of the plunger stop 34. The plunger 88 also includes an elongate arm 114 extending generally parallel to the syringe barrel 84 and configured to engage the needle stop 36 based on a predetermined position of the plunger 88 relative to the syringe barrel 84. The plunger 88 is configured to move the valve stopper 86 toward the fill stopper 90 to dispense medicament or fluid from the syringe barrel 84.

Referring to FIGS. 6 and 7, the syringe assembly 82 also includes a fill cover 116 that seals and encloses the fill stopper 90. The fill cover 116 provides access to the fill stopper 90 during assembly of the device 10. The fill cover 116 is configured to be secured to the housing 12 without being removable by a user of the device 10.

Referring to FIGS. 19-22, the needle stop 36 includes a body 120 that defines a central opening 122 for receiving a pin 124 extending upward from the bottom portion 18 of the housing 12. The body 120 of the needle stop 36 is rotatable about the pin 124 and includes an actuator surface 126 and a plunger surface 128. The actuator surface 126 and the plunger surface 128 are configured to engage the needle actuator 32 and the plunger 88, respectively. The plunger surface 128 is raised and positioned upwardly from the actuator surface 126.

Referring to FIGS. 23-29 and 32, the needle actuator 32 includes an elongate body 132 with a first end 134 and a second end 136. The body 132 of the needle actuator 32 includes a pair of sidewalls 138 extending between the first and second ends 134, 136. The body 132 of the actuator 32 defines an interior space 140 configured to receive a portion of the needle carrier 30. First and second ramp portions 142, 144 extend inward from one of the sidewalls 138 toward the interior space 140. The first ramp portion 142 includes a downward inclined section 146 and a level section 148. The downward inclined section 146 of the first ramp portion 142 extends toward the bottom portion 18 of the housing 12 and towards the second end 136 of the needle actuator 32. The level section 148 is generally parallel to the bottom surface 54 of the bottom portion 18 of the housing 12 and is positioned intermediate the ends 134, 136 of the needle actuator 32. The second ramp portion 144 includes an upward inclined section 150 extending away from the bottom portion 18 of the housing 12 and towards the second end 136 of the needle actuator 32. The second ramp portion 144 also includes a level section 151 that is generally parallel to the bottom surface 54 of the bottom portion 18 of the housing 12. Each of the sidewalls 138 of the needle actuator 32 includes the first and second ramp portions 142, 144, although only one of the sidewalls 138 may be provided with the ramp portions 142, 144. The needle actuator 32 also includes a plunger engagement tab 152 and an indicator tab 154. The plunger engagement tab 152 includes an inclined planar portion 156 that is configured to engage the actuator tab 76 of the plunger stop 34. The plunger engagement tab 152 is disposed adjacent to the first end 134 of the body 132 of the needle actuator 32. The indicator tab 154 includes a planar surface 158 having first and second indicator colors 160, 162. The indicator tab 154 is disposed towards the first end 134 of the body 132 of the needle actuator 32 and is arranged substantially perpendicular to one of the sidewalls 138.

Referring to FIGS. 12, 23-29, and 32, the needle actuator 32 further includes a button engagement 164 extending substantially perpendicular to one of the sidewalls 138 and positioned intermediate the first and second ends 134, 136 of the needle actuator 32. The button engagement 164 is configured to engage the lock member 66 of the activation button 38. Upon downward movement of the activation button 38, the button engagement 164 of the needle actuator 32 is configured to be released from engagement with the lock member 66 of the activation button 38. As shown in FIG. 12, a bottom 165 of the needle actuator 32 defines a bottom opening 166. Further, the needle actuator 32 includes a needle spring 168 disposed within the interior space 140 of the needle actuator 32 and is configured to bias the needle actuator 32 forward toward the first end 14 of the housing 12. The needle actuator 32 also includes a pad 170 disposed within the interior space 140 of the needle actuator 32 and positioned on a bottom surface 172 of the needle actuator 32. The pad 170 is constructed from a rubber material, although other suitable materials may be utilized. Thus, the needle actuator 32 has a first position disposed adjacent to the second end 16 of the housing 12 and a second position disposed adjacent to the first end 14 of the housing 12 with the needle spring 168 configured to move the needle actuator 32 from the first position to the second position.

Figure 9:
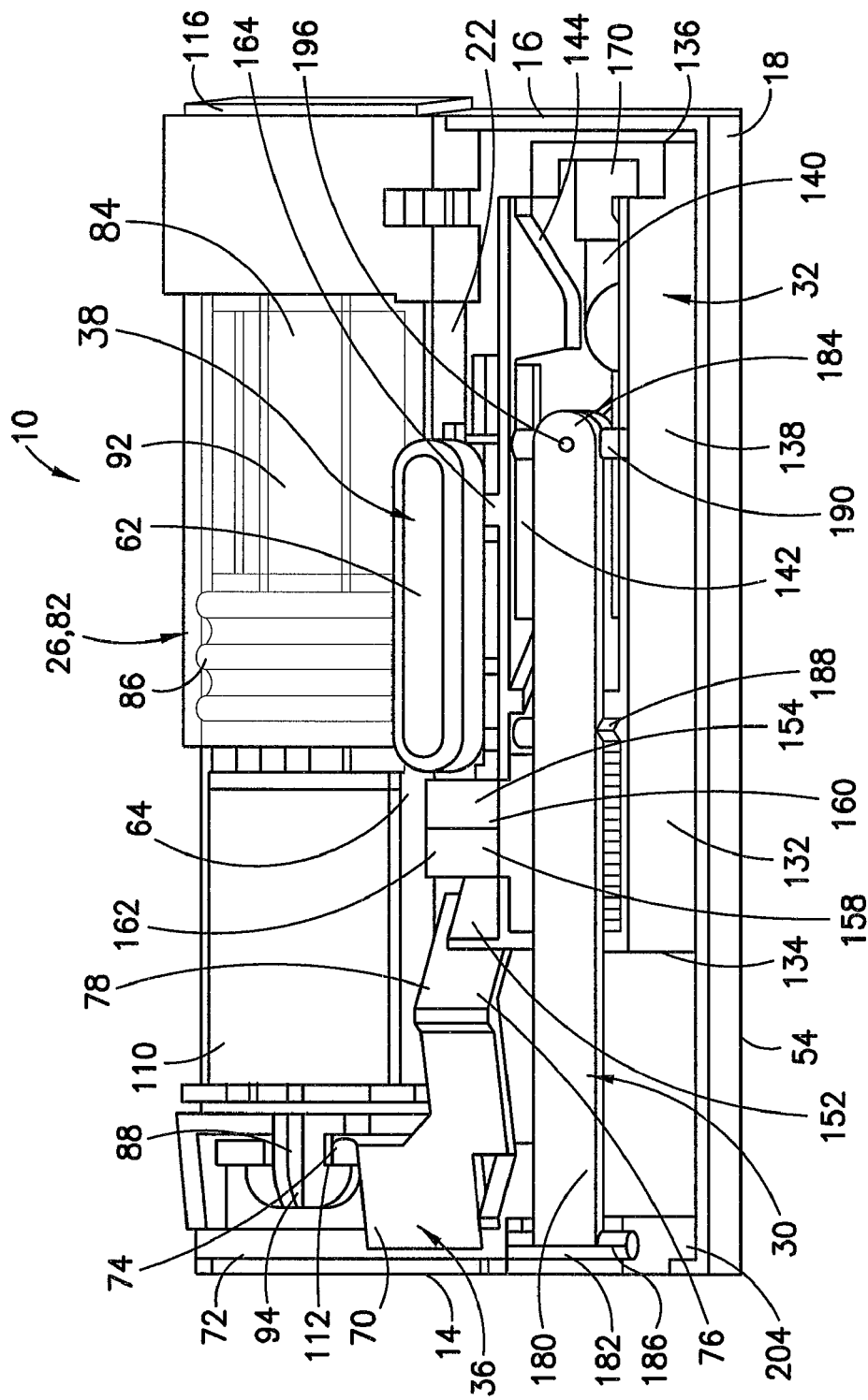
FIG. 9 is a perspective view of the device of FIG. 1 showing a top cover removed in accordance with an embodiment of the present invention.

Referring to FIGS. 9, 10, and 12, the needle carrier 30 includes an elongate body 180 having a first end 182 and a second end 184. The body 180 of the needle carrier 30 includes an attachment member 186 at the first end 182 of the body 180 that is configured to be secured to the bottom portion 18 of the housing 12. The needle carrier 30 is arranged to be generally cantilevered from the attachment member 186 and extending from the first end 14 of the housing 12 towards the second end 16 of the housing 12. A portion of the needle carrier 30 is configured to be received by and engaged with the needle actuator 32. The needle carrier 30 also includes a first engagement 188 disposed between the ends 182, 184 of the body 180 of the needle carrier 30 and a second engagement 190 disposed adjacent the second end 184 of the body 180 of the needle carrier 30. The first and second engagements 188, 190 extend radially outward from the body 180 and substantially perpendicular to a longitudinal axis of the needle carrier 30. The needle carrier 30 further includes a generally cylindrical needle receiver 192 that receives and engages the injection needle 28. The needle carrier 30 defines a passageway 194 having an inlet 196 that is configured to receive the tubing (not shown) from the outlet 106 of the valve stopper 86 of the syringe assembly 82. A lumen (not shown) of the injection needle 28 is in fluid communication with the passageway 194 and the tubing from the valve stopper 86. The needle carrier 30 is generally flexible or semi-rigid to allow the needle carrier 30 to flex from a non-biased state and return to the non-biased state after flexing.

Referring to FIGS. 9-32, upon assembly of the device 10, the device 10 will be in an initial, pre-use state. As discussed in more detail below, the device 10 has a pre-use state, a use state, and a completed state. In the initial state, the syringe assembly 82 is received by the bottom portion 18 of the housing 12 and generally extends from the first end 14 of the housing 12 to the second end 16 of the housing 12. The medicament is provided within the syringe barrel 84 and the plunger 88 is in a fully retracted position as shown in FIG. 9. The plunger spring 108 engages the bottom portion 18 of the housing 12 and the plunger 88 to bias the plunger 88 and valve stopper 86 towards the fill stopper 90. The valve member 98 arranged within the valve stopper 86 is in a closed position. The attachment portion 72 of the plunger stop 34 is secured to the bottom portion 18 of the housing 12 and allows the plunger stop 34 to rotate relative to the bottom portion 18 of the housing 12. The plunger engagement portion 74 of the plunger stop 34 engages the notch 112 of the plunger 88 to restrict movement of the plunger 88 towards the fill stopper 90. The activation button 38 is in a raised position with the top surface 62 of the body 60 extending through the button opening 46 of the housing 12. The lock member 66 is engaged with the button engagement 164 of the needle actuator 32 and prevents movement of the needle actuator 32. The needle actuator 32 is positioned adjacent to the second end 16 of the housing 12 with the second end 136 of the needle actuator 32 abutting the second end 16 of the housing 12. The needle spring 168 is disposed within the interior space 140 of the needle actuator 32 with a first end 200 of the spring 168 engaging the first end 134 of the needle actuator 32 and a second end 198 of the needle spring 168 engaging a spring seat 202 on the bottom portion 18 of the housing 12. Thus, the needle actuator 32 is biased by the needle spring 168 and configured to move the needle actuator 32 from the second end 16 of the housing 12 to the first end 14 of the housing 12 upon release of the button engagement 164 with the lock member 66 of the activation button 38.

The syringe barrel 84 may be filled with a medicament by any suitable method. In one embodiment, with the fill cover 116 and fill stopper 90 removed from the housing 12, the syringe barrel 84 is filled with medicament. A guide tube (not shown), which has a slightly smaller diameter than the inner diameter of the syringe barrel 84, is used to squeeze and place the fill stopper 90 just above the medicament before retracting and leaving the fill stopper 90 in place. A further method uses a machine or apparatus to engage the top of the syringe barrel 84 and evacuate the syringe barrel 84 to a preset vacuum. When the preset vacuum is reached, the fill stopper 90 is pushed down into the syringe barrel 84 and the vacuum is released which causes atmospheric pressure to draw the fill stopper 90 into place while leaving no air gap. Another method of filling the syringe barrel 84 utilizes a piece of wire or string along the outside of the fill stopper 90 while the fill stopper 90 is positioned within the syringe barrel 84. The wire or string creates a temporary break in the seal that allows air to escape from between the fill stopper 90 and the medicament as the fill stopper 90 is pushed into place.

In the initial, pre-use state of the device 10, the needle carrier 30 has a non-biased position with the elongate body 180 of the needle carrier 30 being substantially planar. The attachment member 186 of the needle carrier 30 is rotatably secured to a carrier seat 204 extending upwardly from the bottom portion 18 of the housing 12. A portion of the needle carrier 30 is disposed within the needle actuator 32 with the elongate body 180 of the needle carrier 30 extending substantially parallel to the needle actuator 32. The first engagement 188 of the needle carrier 30 is positioned adjacent to the first ramp portion 142 of the needle actuator 32. The plunger engagement tab 152 of the needle actuator 32 is positioned adjacent to the actuator tab 76 of the plunger stop 34. Further, the indicator tab 154 of the needle actuator 32 is positioned such that the first indicator color 160 is visible through the first indicator lens 48 of the housing 12 to indicate that the device 10 is ready to use.

Referring to FIGS. 14 and 15, after removing the needle cap 58 from the needle opening 56 in the bottom portion 18 of the housing 12 and depressing the activation button 38 to move the activation button 38 further within the housing 12, the device 10 transitions from the pre-use position to the use position. After pressing the activation button 38, the lock member 66 of the activation button 38 is released from the button engagement 164 of the needle actuator 32 to allow forward movement of the needle actuator 32 towards the first end 14 of the housing 12. The needle actuator 32 moves forward, as shown in FIG. 14, and the plunger engagement tab 152 of the needle actuator 32 engages the actuator tab 76 of the plunger stop 34 thereby causing the plunger stop 34 to rotate downward to the position shown in FIG. 15. After the plunger stop 34 has rotated downward a sufficient distance, the plunger engagement portion 74 of the plunger stop 34 is released from the notch 112 of the plunger 88 thereby allowing the plunger 88 to be moved toward the fill stopper 90 by the plunger spring 108. Upon movement of the plunger 88, the valve member 98 within the valve stopper 86 is moved to the open position to place the injection needle 28 in fluid communication with the syringe barrel 84. In particular, in the pre-use position, the plunger 88 is moveable within the valve stopper 86 a predetermined distance. When the plunger 88 disengages from the plunger stop 34, the plunger 88 moves within the valve stopper 86 and causes the valve member 98 to move to the open position. Movement of the valve stopper 86 toward the fill stopper 90 causes fluid within the syringe barrel 84 to move through the passageway 102 in the valve stopper 86 through the tubing (not shown) and through the lumen of the injection needle 28.

Figure 23:
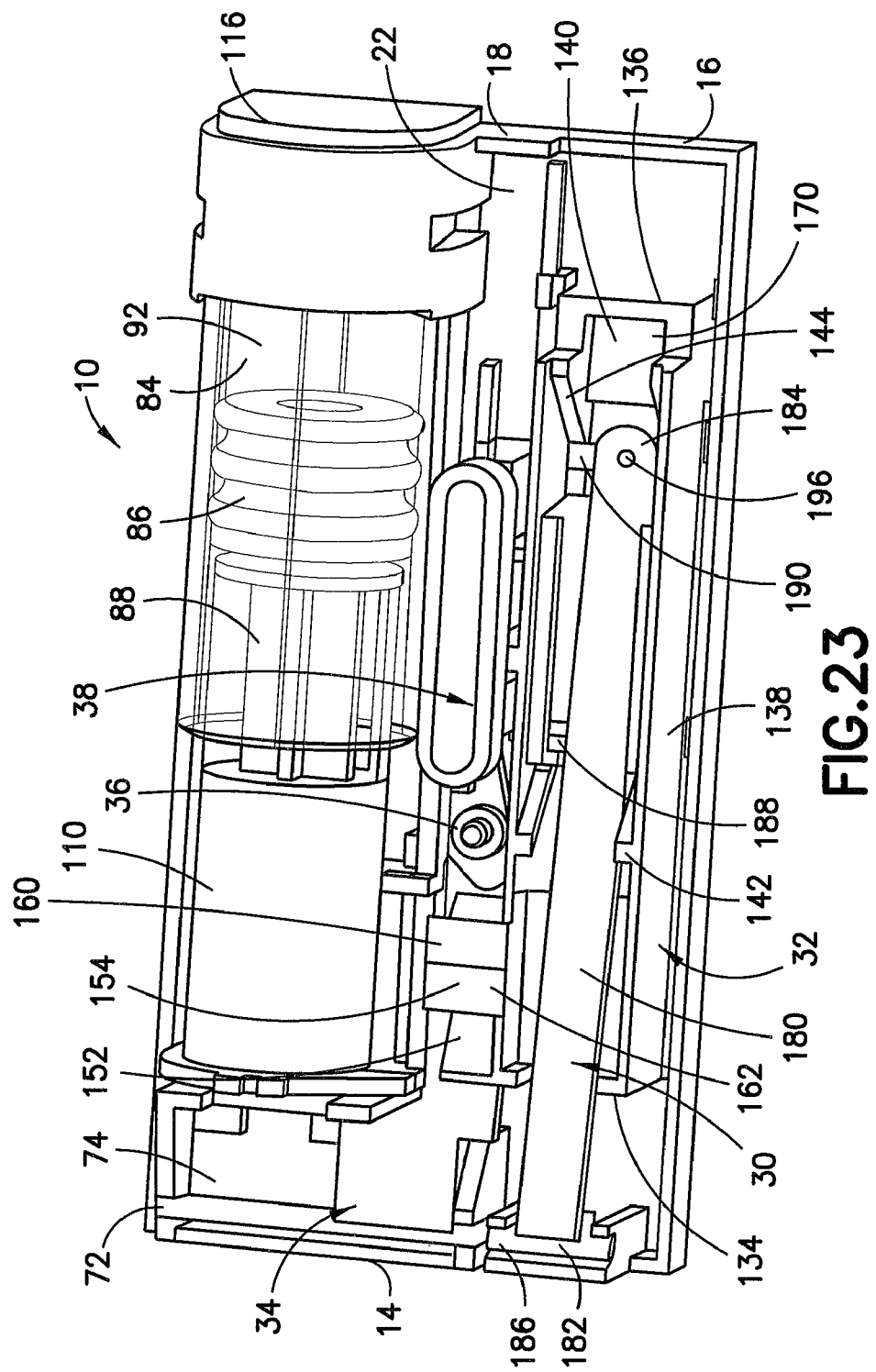
FIG. 23 is a top perspective view of the device of FIG. 1 showing a use position of an injector needle in accordance with an embodiment of the present invention.
Figure 24:
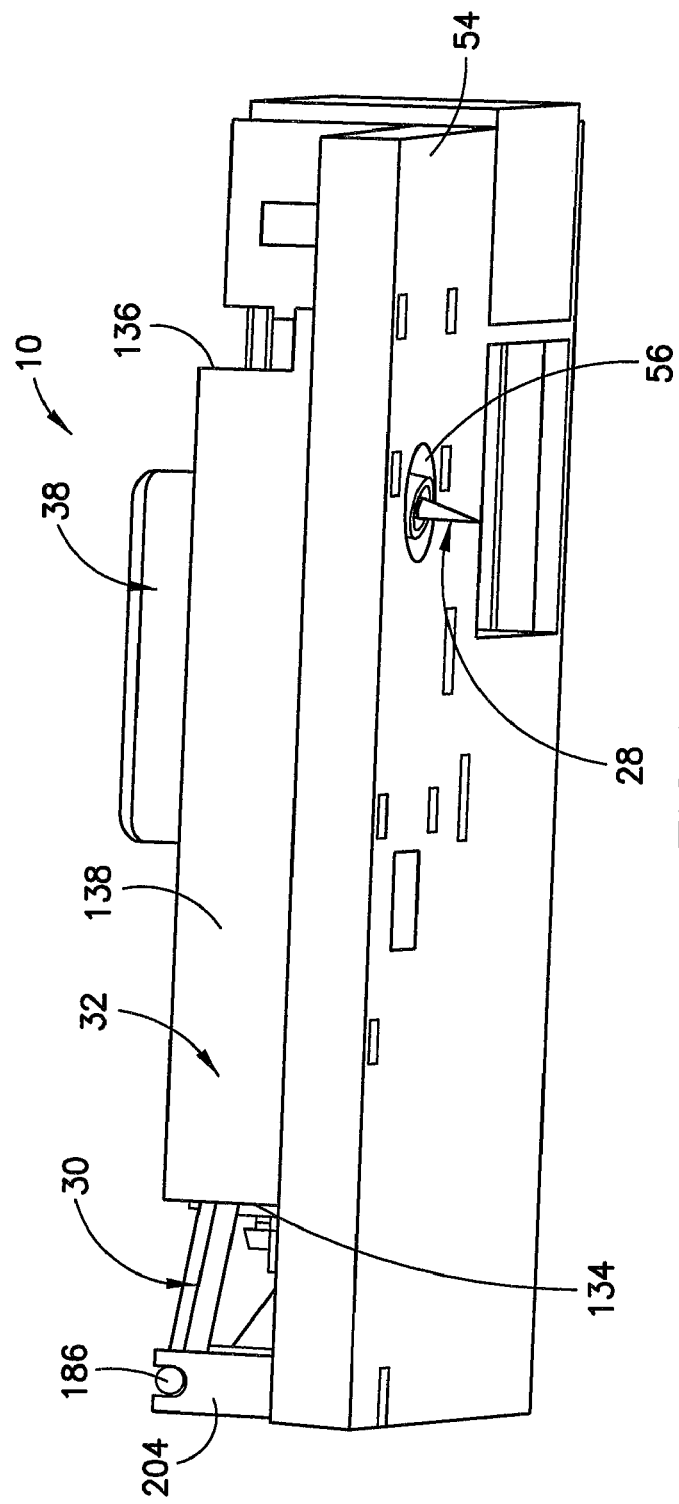
FIG. 24 is a bottom perspective view of the device of FIG. 1 showing a use position of an injector needle in accordance with an embodiment of the present invention.

Referring to FIGS. 23 and 24, when the device 10 is transitioned to the use state from the pre-use state, the injection needle 28 is moved to a use position where the injection needle 28 extends through the needle opening 56 in the bottom portion 18 of the housing 12. In use, the bottom surface 54 of the bottom portion 18 of the housing 12 will be arranged against a target surface of a patient's body such that the injection needle 28 pierces the target surface of the patient. As discussed above, when the injection needle 28 is moved from the initial position to the use position, fluid within the syringe barrel 84 is automatically supplied to the lumen of the injection needle 28 for infusion into the patient.

Figure 29:
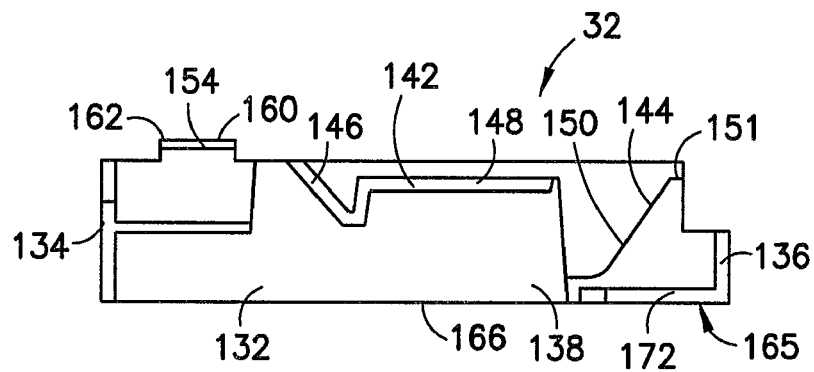
FIG. 29 is a cross-sectional view of a needle actuator in accordance with an embodiment of the present invention.
Figure 30:
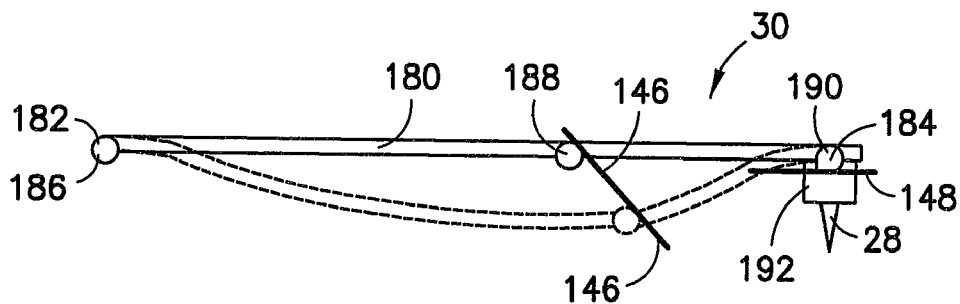
FIG. 30 is a schematic view of a needle carrier showing a pre-loaded position of the needle carrier just prior to movement of an injection needle to a use position in accordance with an embodiment of the present invention.

Referring to FIGS. 29 and 30, during the transition of the injection needle 28 from the initial position to the use position, the needle carrier 30 is pre-loaded to snap the needle carrier 30 downward to quickly pierce the target area of a patient's body with the injection needle 28. In particular, as the needle actuator 32 moves forward toward the first end 14 of the housing 12, the first engagement 188 of the needle carrier 30 engages the bottom of the inclined section 146 of the first ramp portion 142 while the second engagement 190 of the needle carrier 30 engages the top of the level section 148 of the first ramp portion 142. Further movement of the needle actuator 32 causes the intermediate portion between the first and second ends 182, 184 of the needle carrier 30 to flex, as shown in FIG. 30, while the second end 184 of the needle carrier 30 is supported by the level section 148 of the first ramp portion 142. Continued movement of the needle actuator 32 causes the second engagement 190 of the needle carrier 30 to extend beyond the level section 148 of the first ramp portion 142 thereby releasing the second end 184 of the needle carrier 30 and causing the needle carrier 30 and injection needle 28 to snap downwardly.

Referring to FIG. 23, when the device 10 is in the use state and the injection needle 28 is in the use position, the needle carrier 30 is positioned between the first and second ends 14, 16 of the housing 12. The first indicator color 160 of the indicator tab 154 is positioned below the second indicator lens 50 of the housing 12 to indicate that the device 10 is in the use state.

Figure 19:
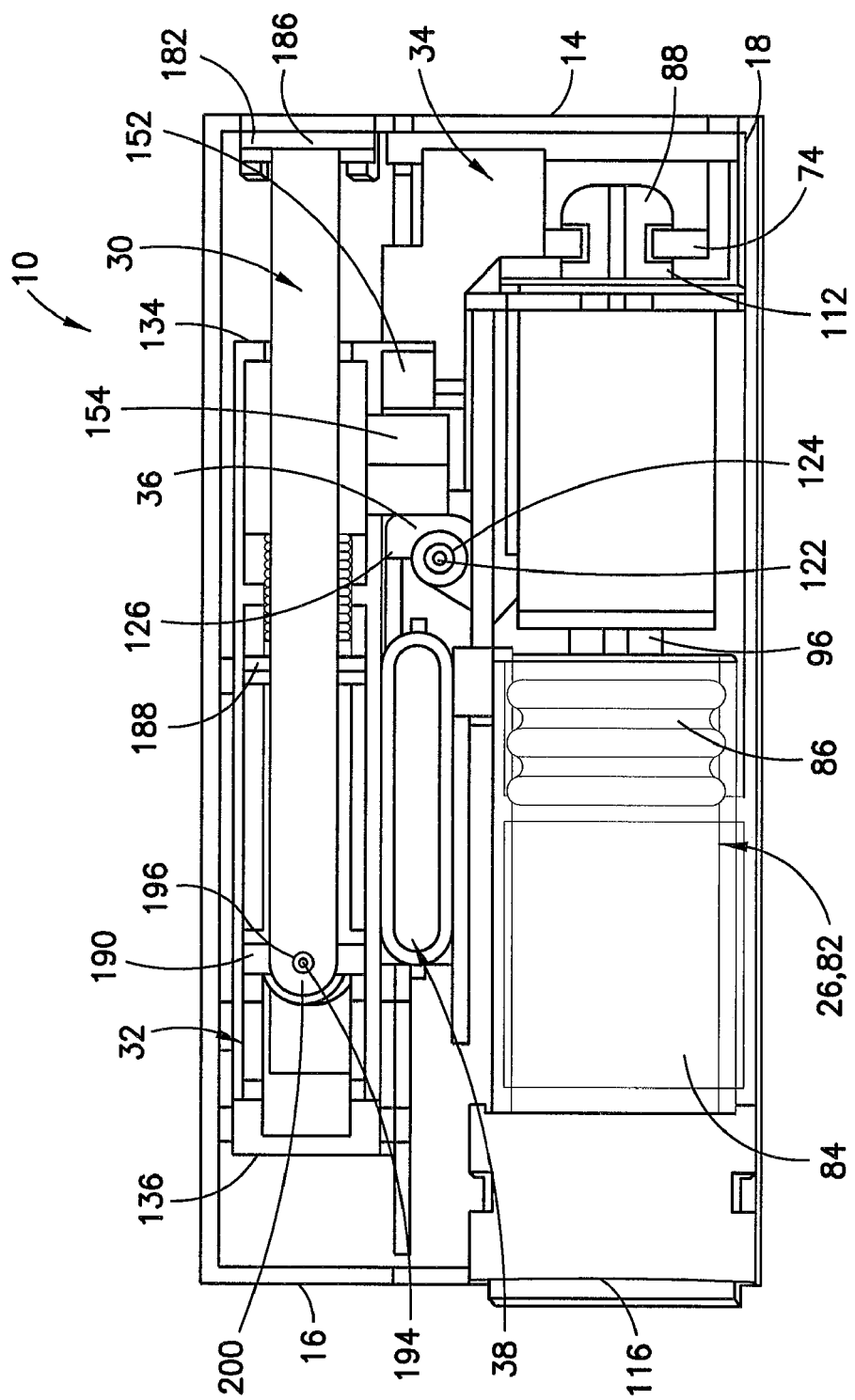
FIG. 19 is a top view of the device of FIG. 1 showing engagement between a needle stop and needle actuator in accordance with an embodiment of the present invention.
Figure 20:
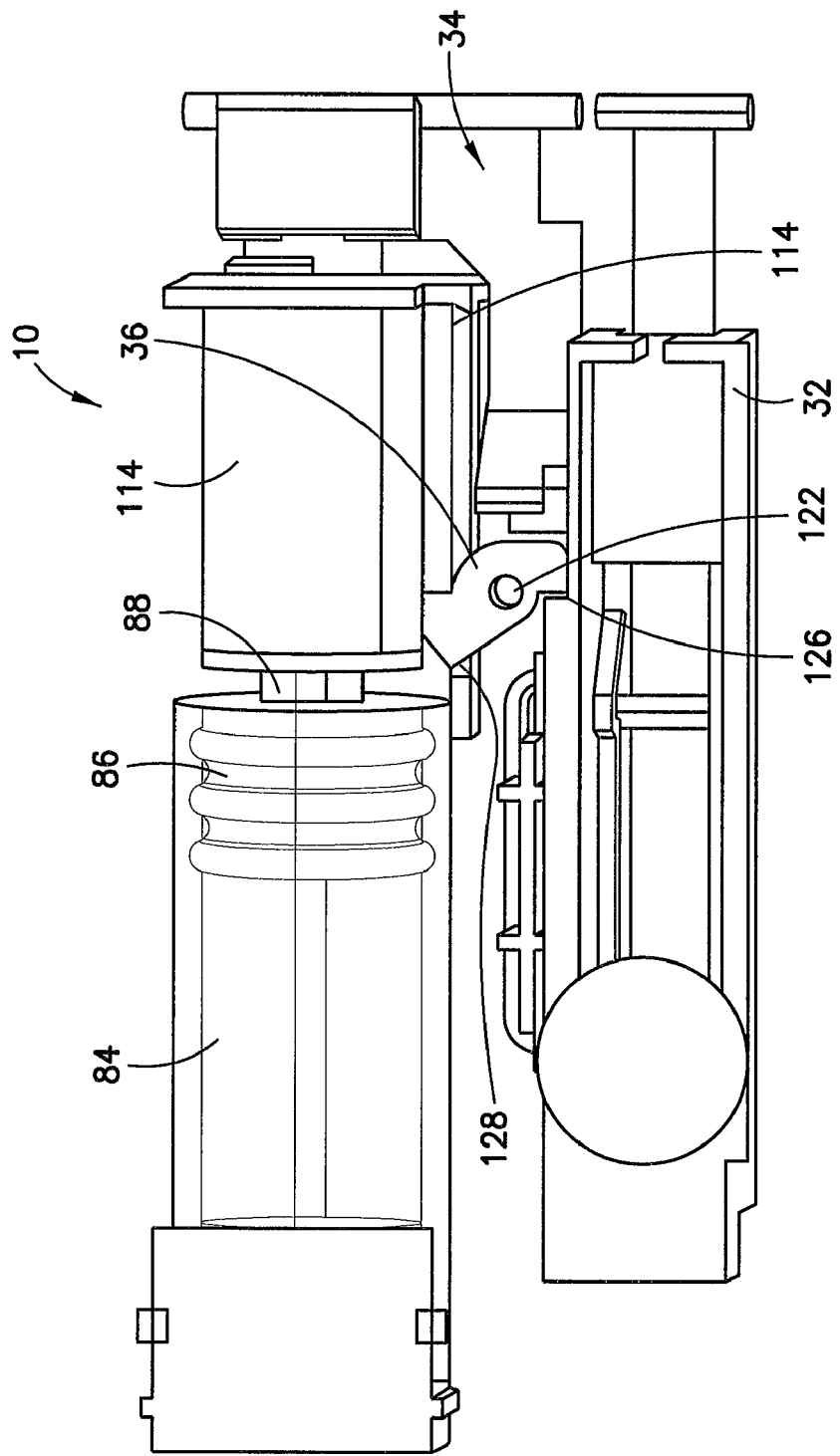
FIG. 20 is a partial bottom view of the device of FIG. 1 showing engagement between a needle stop and plunger in accordance with an embodiment of the present invention.

Referring to FIGS. 19 and 20, continued movement of the needle actuator 32 is restricted when the device 10 is in the use state until a predetermined amount of medicament has been dispensed from the syringe barrel 84. In particular, the actuator surface 126 of the needle stop 36 engages the needle actuator 32 and the plunger surface 128 engages the elongate arm 114 of the plunger 88. The needle stop 36 is restricted from rotating when the needle actuator 32 engages the needle stop 36 due to the interference of the plunger surface 128 of the needle stop 36 with the elongate arm 114 of the plunger 88. Upon further movement of the plunger 88, such as when the valve stopper 86 engages the fill stopper 90, the plunger surface 128 of the needle stop 36 will be free from interference with the elongate arm 114 of the plunger 88 to allow the needle actuator 32 to rotate the needle stop 36 and continue movement of the needle actuator 32 toward the first end 14 of the housing 12.

Figure 21:
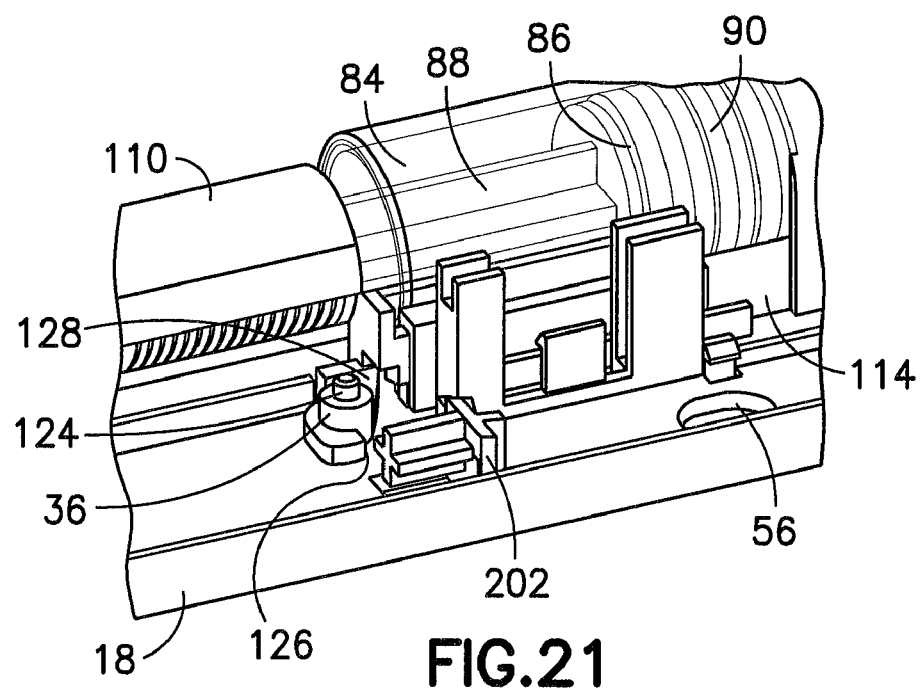
FIG. 21 is a partial perspective view of the device of FIG. 1 showing a needle actuator removed and a plunger in an extended position in accordance with an embodiment of the present invention.
Figure 22:
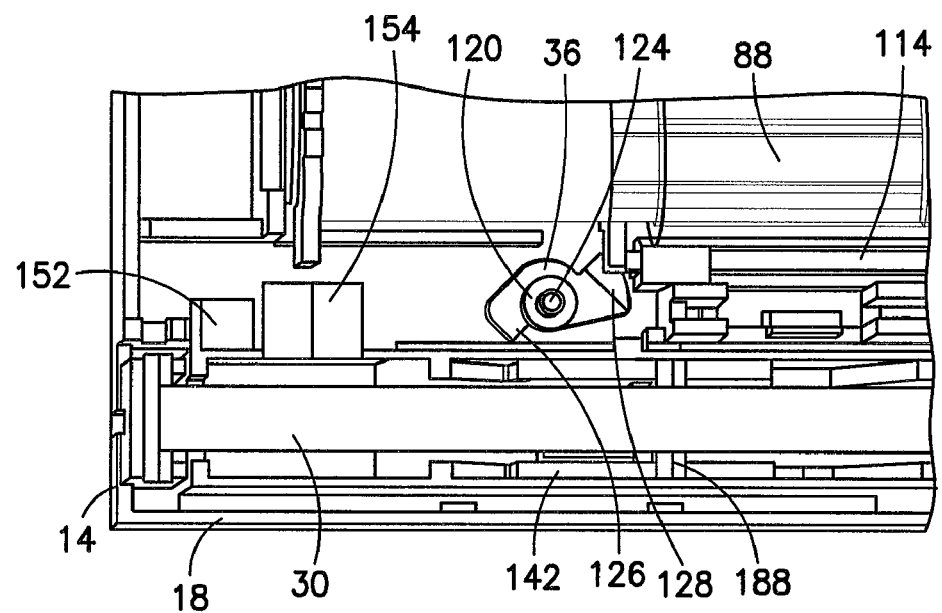
FIG. 22 is a partial top view of the device of FIG. 1 showing a rotated position of a needle stop in accordance with an embodiment of the present invention.
Figure 25:
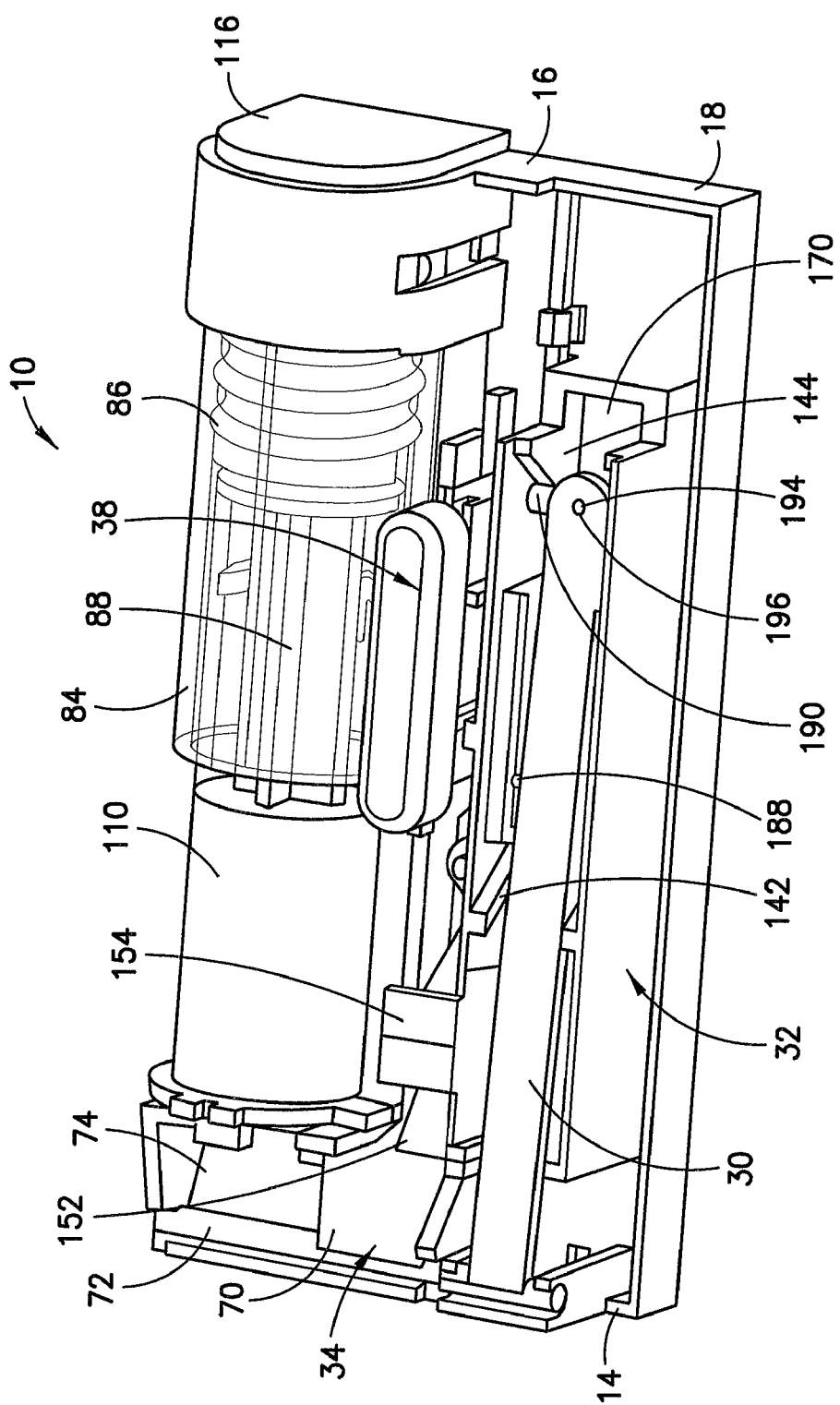
FIG. 25 is a perspective view of the device of FIG. 1 showing an injector needle transitioning from a use position to a shielded position in accordance with an embodiment of the present invention.
Figure 26:
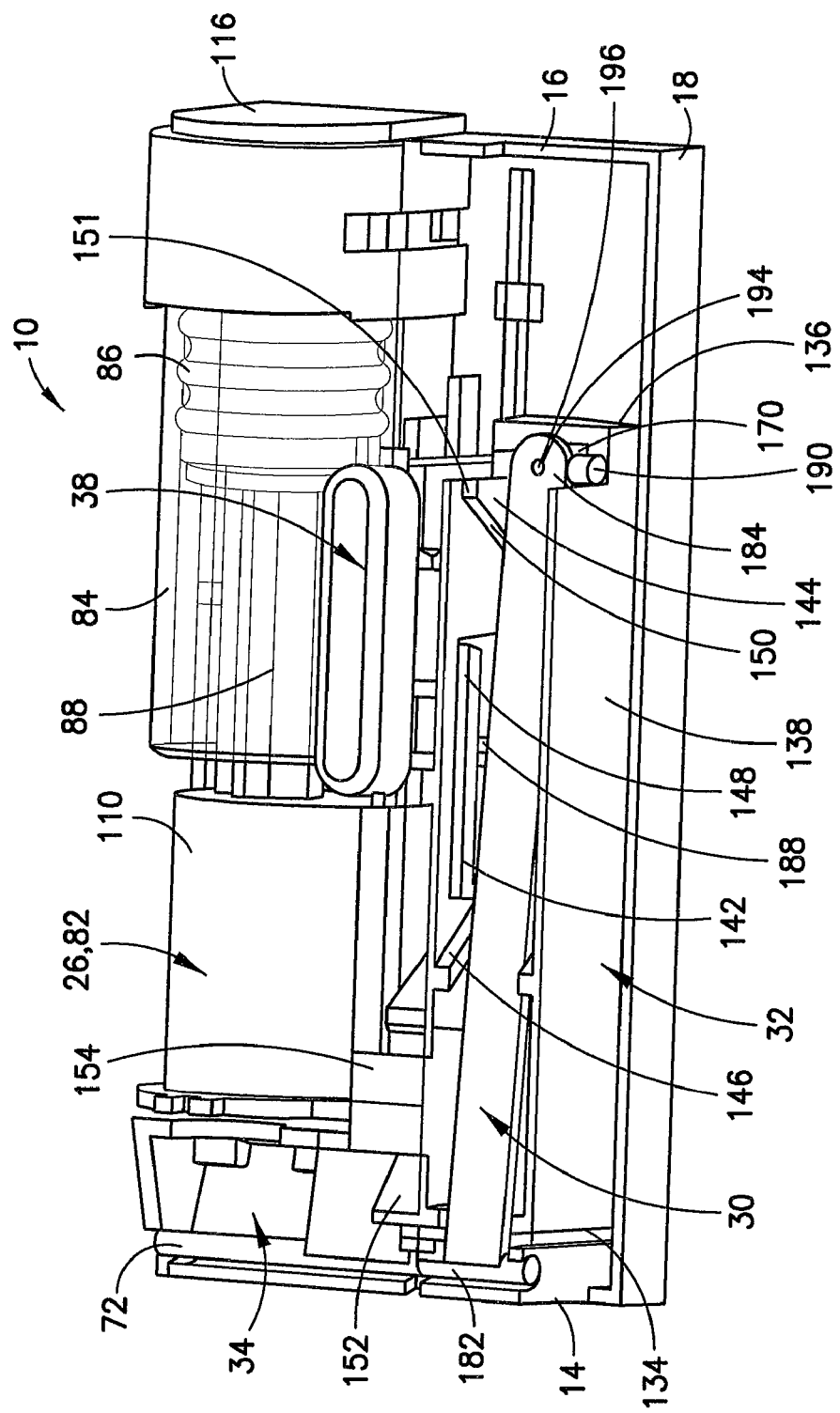
FIG. 26 is a perspective view of the device of FIG. 1 showing an injector needle in a shielded position in accordance with an embodiment of the present invention.
Figure 27:
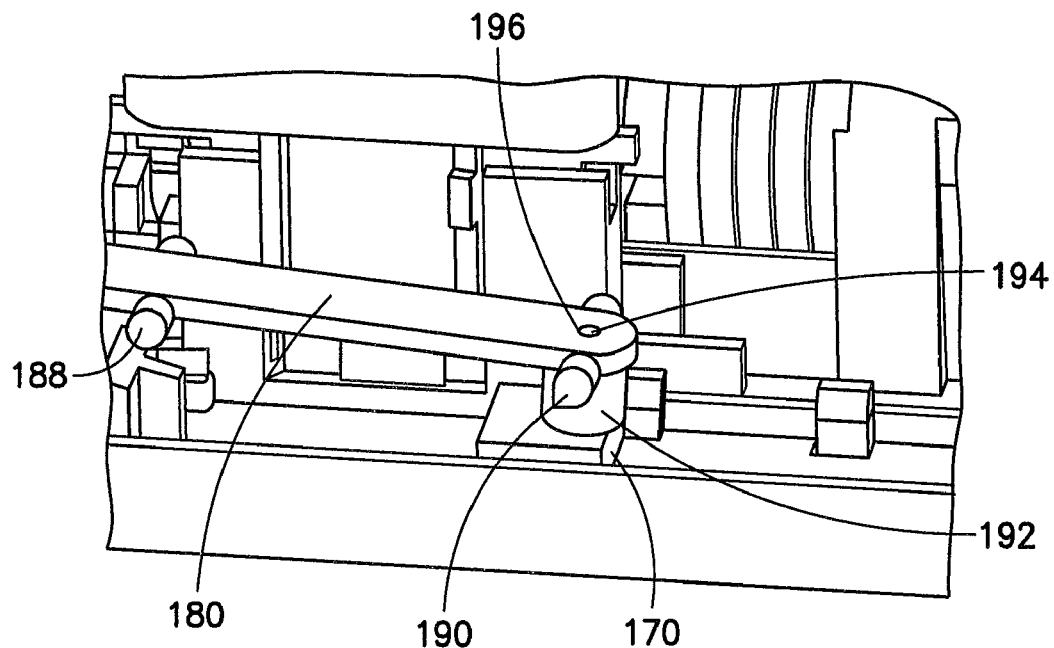
FIG. 27 is a partial perspective view of the device of FIG. 1 showing an injector needle in a shielded position with a needle actuator removed in accordance with an embodiment of the present invention.
Figure 28:
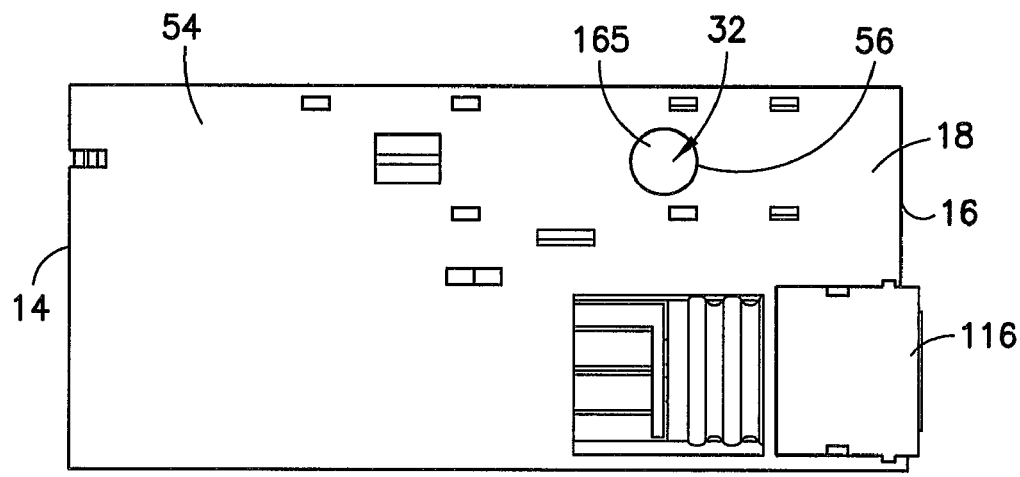
FIG. 28 is a bottom view of the device of FIG. 1 showing an injector needle in a shielded position in accordance with an embodiment of the present invention.

Referring to FIGS. 21, 22, and 25-28, as the needle actuator 32 is moved past the needle stop 36 toward the first end 14 of the housing 12, the device 10 is transitioned from the use state to the completed state. As discussed above, after the plunger 88 moves the valve stopper 86 into engagement with the fill stopper 90 after a predetermined amount of time, the needle stop 36 rotates and allows the needle actuator 32 to move to the first end 14 of the housing 12 with the first end 134 of the needle actuator 32 abutting the first end 14 of the housing 12, as shown in FIG. 26. The rotation of the needle stop 36 and the clearing of the elongate arm 114 of the plunger 88 is shown in FIGS. 21 and 22. The injection needle 28 is transitioned from the use position to the shielded position where the lumen of the injection needle 28 is blocked and where the injection needle 28 is positioned within the housing 12. In particular, in the shielded position, the injection needle 28 engages the pad 170 positioned within the needle actuator 32 to block the lumen of the injection needle 28 and prevent fluid from exiting the injection needle 28. In the completed state of the device, the second indicator color 162 of the indicator tab 154 of the needle actuator 32 is positioned below the third indicator lens 52 of the housing 12 to indicate the completed state of the device 10. Further, as shown in FIG. 28, the bottom 165 of the needle actuator 32 closes the needle opening 56 in the bottom portion 18 of the housing 12.

Figure 31:
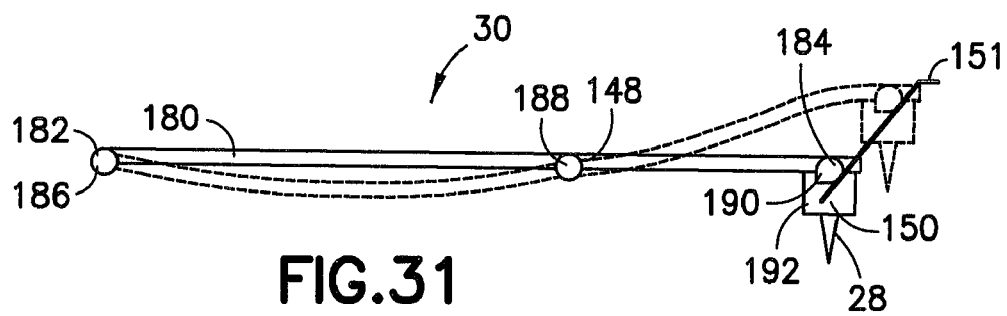
FIG. 31 is a schematic view of a needle carrier showing a pre-loaded position of the needle carrier just prior to movement of an injection needle to a shielded position in accordance with an embodiment of the present invention.
Figure 32:
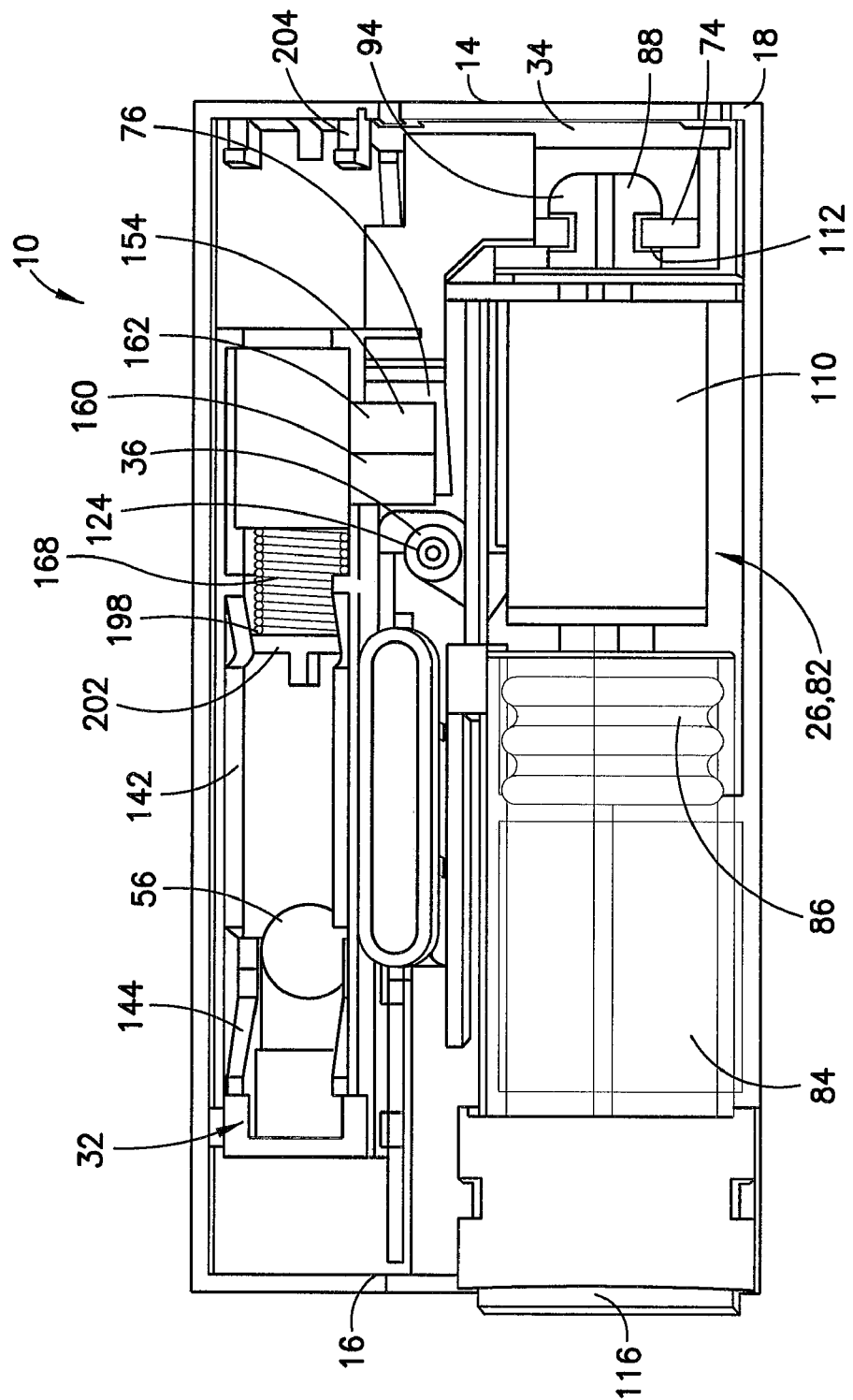
FIG. 32 is a top view of the device of FIG. 1 showing a needle carrier removed in accordance with an embodiment of the present invention.
Figure 33:
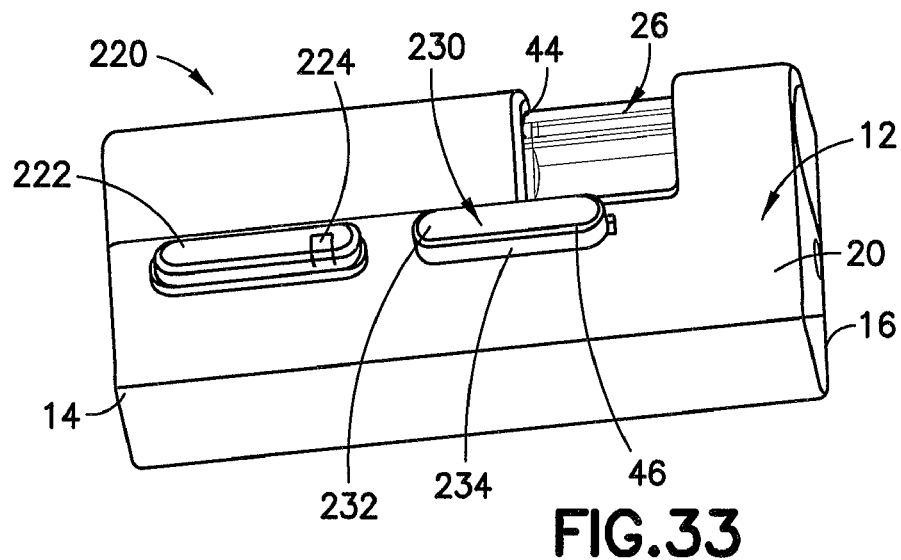
FIG. 33 is a perspective view of a device for delivering a fluid into a patient by injection in accordance with a further embodiment of the present invention.
Figure 34:
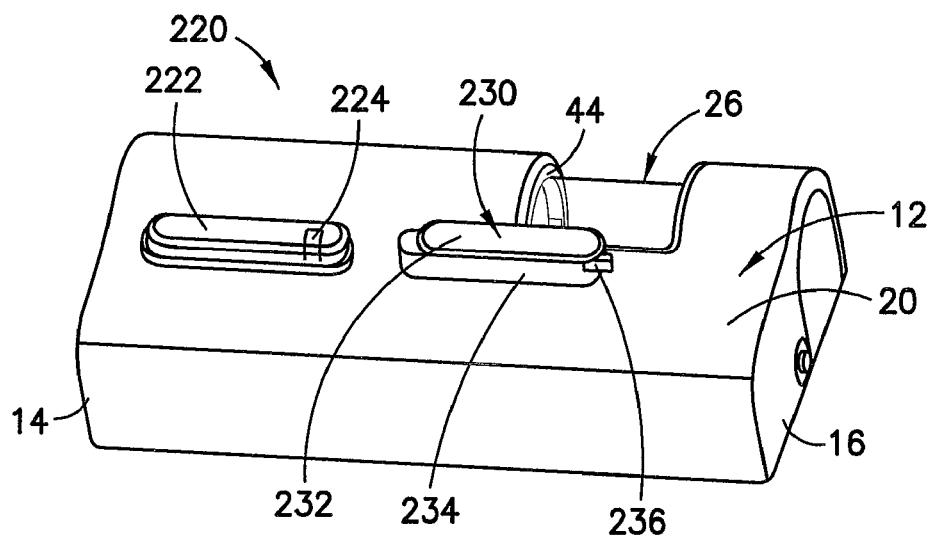
FIG. 34 is a perspective view of the device of FIG. 33 showing button lock in a second position in accordance with a further embodiment of the present invention.
Figure 35:
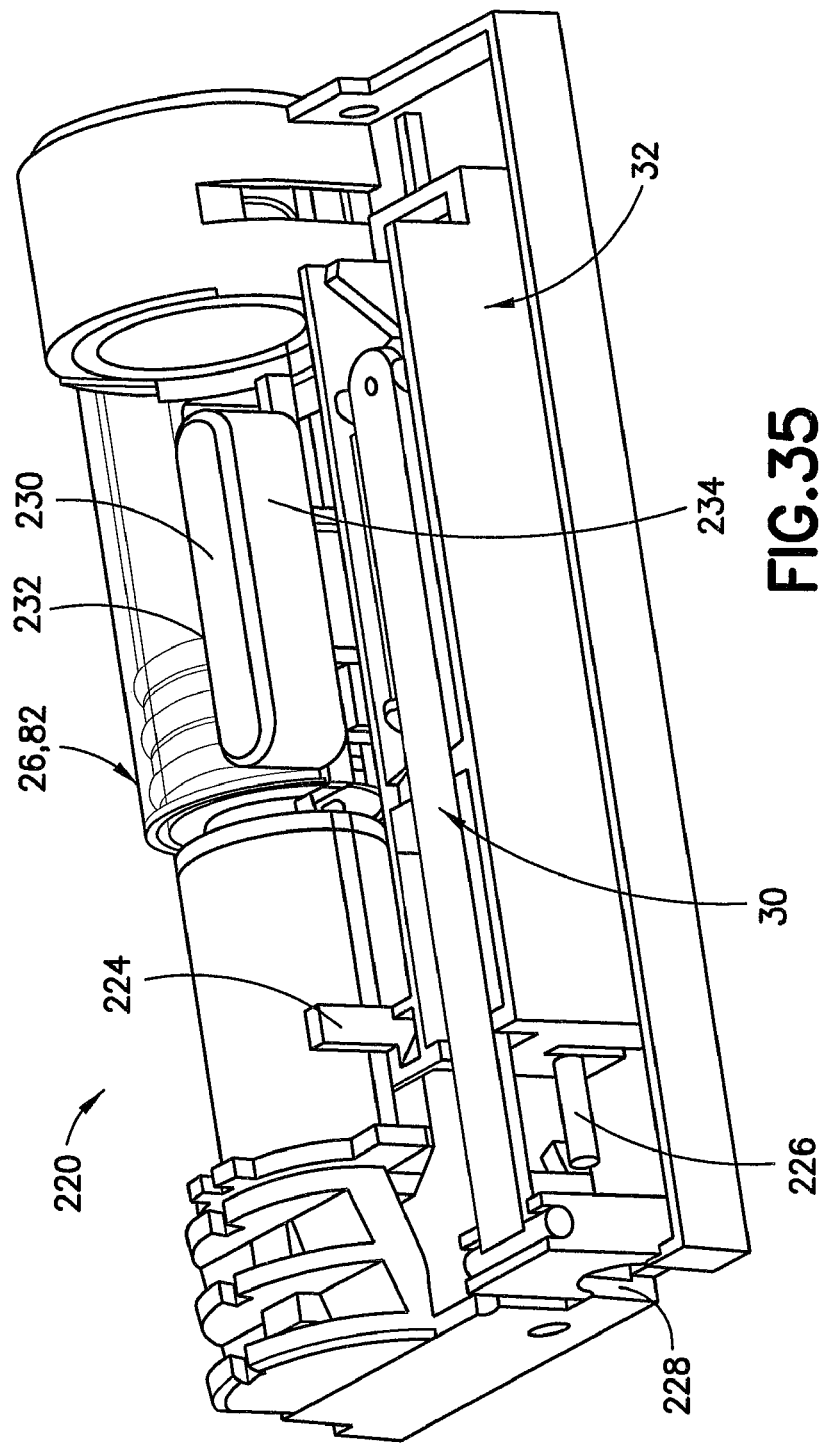
FIG. 35 is a perspective view of the device of FIG. 33 showing a top cover removed in accordance with a further embodiment of the present invention.
Figure 36:
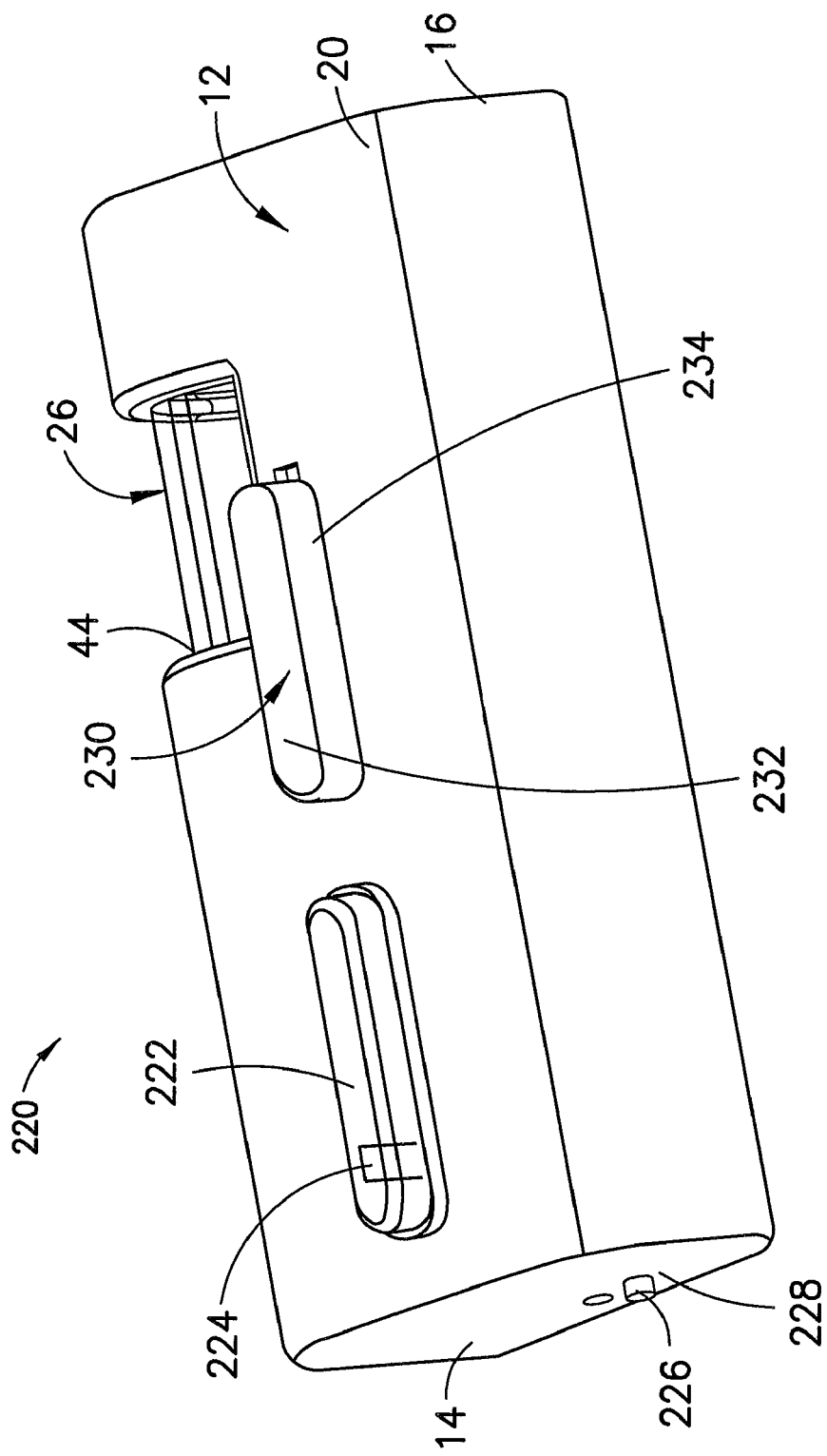
FIG. 36 is a perspective view of the device of FIG. 33 showing the device at the end of an injection cycle in accordance with a further embodiment of the present invention.

Referring to FIGS. 25, 29, and 31, during the transition of the injection needle 28 from the use position to the shielded position, the needle carrier 30 is pre-loaded to snap the needle carrier 30 downward to engage the pad 170 positioned within the needle actuator 32. As the needle actuator 32 moves forward toward the first end 14 of the housing 12, the first engagement 188 of the needle carrier 30 engages the bottom of the level section 148 of the first ramp portion 142 while the second engagement 190 of the needle carrier 30 engages the top of the inclined section 150 of the second ramp portion 144. Further movement of the needle actuator 32 causes the second end 184 of the needle carrier 30 to flex upwardly as the second engagement 190 proceeds along the inclined section 150 of the second ramp portion 144 while the first engagement 188 slides along the level section 148 of the first ramp portion 142. Continued movement of the needle actuator 32 towards the first end 14 of the housing 12 causes the second engagement 190 of the needle carrier 30 to extend beyond the level section 151 of the second ramp portion 144 thereby causing the needle carrier 30 and injection needle 28 to snap downwardly into the pad 170.

After the injection needle 28 engages the pad 170, the lumen of the injection needle 28 is blocked by the pad 170 to prevent fluid from leaking out of the device 10 when the device 10 is in the completed state.

Referring to FIGS. 33-36, a second embodiment of a device 220 for delivering a fluid into a patient by injection is shown. The device 220 is similar to the device 10 shown in FIGS. 1-32, expect for the differences discussed below. Like reference numbers are used for like elements. Instead of providing the first, second, and third indicator lenses 48, 50, 52, the device 220 shown in FIGS. 33-36 includes an indicator lens 222 that extends outward from the top cover 20 of the housing 12. Further, the needle actuator 32 includes a raised indicator tab 224 that extends upwardly from the body 132 of the needle actuator 32. The raised indicator tab 224 of the needle actuator 32 extends into the indicator lens 222 and is received by the indicator lens 222. The needle actuator 32 also includes an indicator post 226 that extends outward from the first end 134 of the needle actuator 32. The first end 14 of the housing 12 defines an indicator opening 228 configured to receive the indicator post 226. As the device 220 is moved from the pre-use state, the use state, and the completed state, the indicator tab 224 on the needle actuator 32 will move within the indicator lens 222 to provide an indication of the state of the device 220. Further, when the device 220 is in the completed state, the indicator post 226 of the needle actuator 32 will protrude through the indicator opening 228 of the housing 12 to provide visual and tactile feedback of the completed state of the device 220. The indicator tab 224 and the indicator lens 222 arrangement of the present embodiment allows the indicator tab 224 to be viewed from a larger viewing area compared to the indicator arrangement of the first embodiment.

Referring again to FIGS. 33-36, the device 220 of the second embodiment also includes a two piece activation button 230 having a first portion 232 and a second portion 234. The first portion 232 is moveable relative to the second portion 234 and has a locked position (shown in FIG. 34) and a use position (shown in FIG. 33). When the first portion 232 is in the locked position, a protrusion 236 extends radially outward to interfere with the button opening 46 in the top cover 20 of the housing 12 to prevent the activation button 38 from being depressed. When the first portion 232 of the activation button 230 is moved to the use position, the protrusion 236 is received by the second portion 234 and allows the activation button 230 to be depressed to begin the injection process. The activation button 230, however, otherwise operates in a similar manner as described above in connection with the first embodiment. Accordingly, the two-piece activation button 230 allows the activation button to be locked to prevent accidental operation of the device.

While several embodiments were described in the foregoing detailed description, those skilled in the art may make modifications and alterations to these embodiments without departing from the scope and spirit of the invention. Accordingly, the foregoing description is intended to be illustrative rather than restrictive. The invention described hereinabove is defined by the appended claims and all changes to the invention that fall within the meaning and the range of equivalency of the claims are embraced within their scope.

What is claimed is:

1. A device for delivering a fluid comprising: a housing defining an interior space and having a bottom surface configured for contacting a patient, the bottom surface defining a needle opening; a reservoir disposed within the interior space of the housing for containing a fluid therein;

a needle carrier disposed within the housing; an injection needle supported by the needle carrier and defining a lumen, the lumen of the injection needle configured to be placed in fluid communication with the reservoir, wherein the injection needle is transitionable from an initial position in which the injection needle is disposed within the housing, to a use position in which the injection needle extends through the needle opening, and a shielded position in which the injection needle is disposed within the housing; and a first indicator indicating when the injection needle is in the initial position, a second indicator indicating when the injection needle is in the use position and a third indicator indicating when the injection needle is in the shielded position.

2. The device of claim 1, wherein the housing includes at least one indicator lens, and wherein the indicator is visible from an exterior of the housing via the indicator lens.

3. The device of claim 1, wherein the indicator provides a visual and tactile indication of the position of the injection needle.

4. The device of claim 1, further comprising a needle actuator controlling positioning of the needle carrier and the injection needle;
wherein the indicator comprises at least one indicator lens permitting visual inspection of the needle actuator to separately indicate when the injection needle is in the initial position, the use position, and the shielded position.

5. The device of claim 4, wherein the indicator comprises first through third indicator lenses, each permitting visual inspection of the needle actuator, and respectively indicating when the injection needle is in the initial position, the use position, and the shielded position.

6. The device of claim 4, wherein the indicator comprises an indicator tab disposed on and movable with the needle actuator.

7. A device for delivering a fluid comprising:
a housing defining an interior space and having a bottom surface configured for contacting a patient, the bottom surface defining a needle opening;
a reservoir disposed within the interior space of the housing for containing a fluid therein;
a needle carrier disposed within the housing;
an injection needle supported by the needle carrier and defining a lumen, the lumen of the injection needle configured to be placed in fluid communication with the reservoir, wherein the injection needle is transitionable from an initial position in which the injection needle is disposed within the housing, to a use position in which the injection needle extends through the needle opening, and a shielded position in which the injection needle is disposed within the housing; and
an indicator for separately indicating when the injection needle is in the initial position, the use position and the shielded position;
wherein the indicator comprises an indicator post and the housing defines an indicator opening, the indicator post being disposed within the housing when the injection needle is in the initial position and the use position, the indicator post extending through the indicator opening when the injection needle is in the shielded position.

8. A device for delivering a fluid comprising:
a housing defining an interior space and having a bottom surface configured for contacting a patient, the bottom surface defining a needle opening;
a reservoir disposed within the interior space of the housing for containing a fluid therein;
a needle carrier disposed within the housing;
an injection needle supported by the needle carrier and defining a lumen, the lumen of the injection needle configured to be placed in fluid communication with the reservoir, wherein the injection needle is transitionable from an initial position in which the injection needle is disposed within the housing, to a use position in which the injection needle extends through the needle opening, and a shielded position in which the injection needle is disposed within the housing;
a needle actuator controlling positioning of the needle carrier and the injection needle; and
an indicator for separately indicating when the injection needle is in the initial position, the use position, and the shielded position;
wherein the needle actuator closes the needle opening when the injection needle is in the shielded position.

* * * * *

UNITED STATES PATENT AND TRADEMARK OFFICE
CERTIFICATE OF CORRECTION

Page 1 of 1

PATENT NO. : 11,364,336 B2
APPLICATION NO. : 16/523778
DATED : June 21, 2022
INVENTOR(S) : Richard Cronenberg It is certified that error appears in the above-identified patent and that said Letters Patent is hereby corrected as shown below:

On the Title Page:

The first or sole Notice should read --

Subject to any disclaimer, the term of this patent is extended or adjusted under 35 U.S.C. 154(b) by 383 days.

Signed and Sealed this
Eleventh Day of February, 2025

Coke Morgan Stewart
*Acting Director of the United States Patent and Trademark Office*